United States Patent [19]

Lemischka

[11] Patent Number: 5,283,354

[45] Date of Patent: Feb. 1, 1994

[54] NUCLEIC ACIDS ENCODING HEMATOPOIETIC STEM CELLS RECEPTORS FLK-1

[75] Inventor: Ihor R. Lemischka, Princeton, N.J.

[73] Assignee: The Trustees of Princeton University, Princeton, N.J.

[21] Appl. No.: 946,507

[22] Filed: Sep. 17, 1992

Related U.S. Application Data

[60] Division of Ser. No. 813,593, Dec. 24, 1991, Pat. No. 5,185,438, which is a continuation-in-part of Ser. No. 793,065, Nov. 15, 1991, which is a continuation-in-part of Ser. No. 728,913, Jun. 28, 1991, abandoned, which is a continuation-in-part of Ser. No. 679,666, Apr. 2, 1991, abandoned.

[51] Int. Cl.$^5$ ............................................. C07H 21/00
[52] U.S. Cl. ................................. 536/23.5; 435/69.1; 530/350; 530/403
[58] Field of Search ..................... 536/23.5; 530/387.1, 530/350, 846, 403; 514/12; 435/69.1, 172.1, 320.1

[56] References Cited

PUBLICATIONS

A. F. Wilks PNAS 86:1603–1607 Mar. 1989.
W. Matthews et al. PNAS 88:9026–9030 Oct. 1991.
R. Sarzani et al. Biochem Biophys Res Comm. 186(2) 706–714 Jul. 31, 1992.
B. Millauer et al. Cell 72:835–846 1993.
B. Terman et al. Biochem Biophys Res Comm. 187(3) 1579 1992.

*Primary Examiner*—Robert J. Hill, Jr.
*Assistant Examiner*—Lorraine M. Spector
*Attorney, Agent, or Firm*—Irving N. Feit; Eric J. Sheets

[57] ABSTRACT

Isolated mammalian nucleic acid molecules encoding receptor protein tyrosine kinases expressed in primitive hematopoietic cells and not expressed in mature hematopoietic cells are provided. Also included are the receptors encoded by such nucleic acid molecules; the nucleic acid molecules encoding receptor protein tyrosine kinases having the sequences shown in FIG. 1(flk-2) and FIG. 2 (flk-1); the receptor protein tyrosine kinases having the amino acid sequences shown in FIG. 1(flk-2) and FIG. 2 (flk-1); ligands for the receptors; nucleic acid sequences that encode the ligands; and methods of stimulating the proliferation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

3 Claims, 14 Drawing Sheets

Figure 1a.

```
GCGGCCTGGC TACCGCGCGC TCCGGAGGCC ATG CGG GCG TTG GCG CAG CGC AGC
                                    Met Arg Ala Leu Ala Gln Arg Ser
                                     1               5

GAC CGG CGG CTG CTG CTG CTT GTT GTT TTG TCA GTA ATG ATT CTT GAG
Asp Arg Arg Leu Leu Leu Leu Val Val Leu Ser Val Met Ile Leu Glu
        10              15                  20

ACC GTT ACA AAC CAA GAC CTG CCT GTG ATC AAG TGT GTT TTA ATC AGT
Thr Val Thr Asn Gln Asp Leu Pro Val Ile Lys Cys Val Leu Ile Ser
 25              30                  35                      40

CAT GAG AAC AAT GGC TCA TCA GCG GGA AAG CCA TCA TCG TAC CGA ATG
His Glu Asn Asn Gly Ser Ser Ala Gly Lys Pro Ser Ser Tyr Arg Met
                 45                  50                      55

GTG CGA GGA TCC CCA GAA GAC CTC CAG TGT ACC CCG AGG CGC CAG AGT
Val Arg Gly Ser Pro Glu Asp Leu Gln Cys Thr Pro Arg Arg Gln Ser
             60                  65                  70

GAA GGG ACG GTA TAT GAA GCG GCC ACC GTG GAG GTG GCC GAG TCT GGG
Glu Gly Thr Val Tyr Glu Ala Ala Thr Val Glu Val Ala Glu Ser Gly
             75                  80                  85

TCC ATC ACC CTG CAA GTG CAG CTC GCC ACC CCA GGG GAC CTT TCC TGC
Ser Ile Thr Leu Gln Val Gln Leu Ala Thr Pro Gly Asp Leu Ser Cys
         90                  95                  100

CTC TGG GTC TTT AAG CAC AGC TCC CTG GGC TGC CAG CCG CAC TTT GAT
Leu Trp Val Phe Lys His Ser Ser Leu Gly Cys Gln Pro His Phe Asp
105                 110                 115                 120

TTA CAA AAC AGA GGA ATC GTT TCC ATG GCC ATC TTG AAC GTG ACA GAG
Leu Gln Asn Arg Gly Ile Val Ser Met Ala Ile Leu Asn Val Thr Glu
                125                 130                 135

ACC CAG GCA GGA GAA TAC CTA CTC CAT ATT CAG AGC GAA CGC GCC AAC
Thr Gln Ala Gly Glu Tyr Leu Leu His Ile Gln Ser Glu Arg Ala Asn
            140                 145                 150

TAC ACA GTA CTG TTC ACA GTG AAT GTA AGA GAT ACA CAG CTG TAT GTG
Tyr Thr Val Leu Phe Thr Val Asn Val Arg Asp Thr Gln Leu Tyr Val
            155                 160                 165

CTA AGG AGA CCT TAC TTT AGG AAG ATG GAA AAC CAG GAT GCA CTG CTC
Leu Arg Arg Pro Tyr Phe Arg Lys Met Glu Asn Gln Asp Ala Leu Leu
        170                 175                 180

TGC ATC TCC GAG GGT GTT CCG GAG CCC ACT GTG GAG TGG GTG CTC TGC
Cys Ile Ser Glu Gly Val Pro Glu Pro Thr Val Glu Trp Val Leu Cys
185                 190                 195                 200

AGC TCC CAC AGG GAA AGC TGT AAA GAA GAA GGC CCT GCT GTT GTC AGA
Ser Ser His Arg Glu Ser Cys Lys Glu Glu Gly Pro Ala Val Val Arg
                205                 210                 215

AAG GAG GAA AAG GTA CTT CAT GAG TTG TTC GGA ACA GAC ATC AGA TGC
Lys Glu Glu Lys Val Leu His Glu Leu Phe Gly Thr Asp Ile Arg Cys
                220                 225                 230
```

Figure 1b.

```
TGT GCT AGA AAT GCA CTG GGC CGC GAA TGC ACC AAG CTG TTC ACC ATA
Cys Ala Arg Asn Ala Leu Gly Arg Glu Cys Thr Lys Leu Phe Thr Ile
        235             240             245

GAT CTA AAC CAG GCT CCT CAG AGC ACA CTG CCC CAG TTA TTC CTG AAA
Asp Leu Asn Gln Ala Pro Gln Ser Thr Leu Pro Gln Leu Phe Leu Lys
        250             255             260

GTG GGG GAA CCC TTG TGG ATC AGG TGT AAG GCC ATC CAT GTG AAC CAT
Val Gly Glu Pro Leu Trp Ile Arg Cys Lys Ala Ile His Val Asn His
265             270             275             280

GGA TTC GGG CTC ACC TGG GAG CTG GAA GAC AAA GCC CTG GAG GAG GGC
Gly Phe Gly Leu Thr Trp Glu Leu Glu Asp Lys Ala Leu Glu Glu Gly
                285             290             295

AGC TAC TTT GAG ATG AGT ACC TAC TCC ACA AAC AGG ACC ATG ATT CGG
Ser Tyr Phe Glu Met Ser Thr Tyr Ser Thr Asn Arg Thr Met Ile Arg
            300             305             310

ATT CTC TTG GCC TTT GTG TCT TCC GTG GGA AGG AAC GAC ACC GGA TAT
Ile Leu Leu Ala Phe Val Ser Ser Val Gly Arg Asn Asp Thr Gly Tyr
        315             320             325

TAC ACC TGC TCT TCC TCA AAG CAC CCC AGC CAG TCA GCG TTG GTG ACC
Tyr Thr Cys Ser Ser Ser Lys His Pro Ser Gln Ser Ala Leu Val Thr
        330             335             340

ATC CTA GAA AAA GGG TTT ATA AAC GCT ACC AGC TCG CAA GAA GAG TAT
Ile Leu Glu Lys Gly Phe Ile Asn Ala Thr Ser Ser Gln Glu Glu Tyr
345             350             355             360

GAA ATT GAC CCG TAC GAA AAG TTC TGC TTC TCA GTC AGG TTT AAA GCG
Glu Ile Asp Pro Tyr Glu Lys Phe Cys Phe Ser Val Arg Phe Lys Ala
                365             370             375

TAC CCA CGA ATC CGA TGC ACG TGG ATC TTC TCT CAA GCC TCA TTT CCT
Tyr Pro Arg Ile Arg Cys Thr Trp Ile Phe Ser Gln Ala Ser Phe Pro
            380             385             390

TGT GAA CAG AGA GGC CTG GAG GAT GGG TAC AGC ATA TCT AAA TTT TGC
Cys Glu Gln Arg Gly Leu Glu Asp Gly Tyr Ser Ile Ser Lys Phe Cys
        395             400             405

GAT CAT AAG AAC AAG CCA GGA GAG TAC ATA TTC TAT GCA GAA AAT GAT
Asp His Lys Asn Lys Pro Gly Glu Tyr Ile Phe Tyr Ala Glu Asn Asp
        410             415             420

GAC GCC CAG TTC ACC AAA ATG TTC ACG CTG AAT ATA AGA AAG AAA CCT
Asp Ala Gln Phe Thr Lys Met Phe Thr Leu Asn Ile Arg Lys Lys Pro
425             430             435             440

CAA GTG CTA GCA AAT GCC TCA GCC AGC CAG GCG TCC TGT TCC TCT GAT
Gln Val Leu Ala Asn Ala Ser Ala Ser Gln Ala Ser Cys Ser Ser Asp
                445             450             455

GGC TAC CCG CTA CCC TCT TGG ACC TGG AAG AAG TGT TCG GAC AAA TCT
Gly Tyr Pro Leu Pro Ser Trp Thr Trp Lys Lys Cys Ser Asp Lys Ser
            460             465             470
```

Figure 1c.

| | | | | | | | | | | | | | |
|---|---|---|---|---|---|---|---|---|---|---|---|---|---|
| CCC | AAT | TGC | ACG | GAG | GAA | ATC | CCA | GAA | GGA | GTT | TGG | AAT | AAA AAG GCT |
| Pro | Asn | Cys | Thr | Glu | Glu | Ile | Pro | Glu | Gly | Val | Trp | Asn | Lys Lys Ala |
| | | 475 | | | | 480 | | | | | | 485 | |

```
CCC AAT TGC ACG GAG GAA ATC CCA GAA GGA GTT TGG AAT AAA AAG GCT
Pro Asn Cys Thr Glu Glu Ile Pro Glu Gly Val Trp Asn Lys Lys Ala
        475             480                     485

AAC AGA AAA GTG TTT GGC CAG TGG GTG TCG AGC AGT ACT CTA AAT ATG
Asn Arg Lys Val Phe Gly Gln Trp Val Ser Ser Ser Thr Leu Asn Met
        490             495             500

AGT GAG GCC GGG AAA GGG CTT CTG GTC AAA TGC TGT GCG TAC AAT TCT
Ser Glu Ala Gly Lys Gly Leu Leu Val Lys Cys Cys Ala Tyr Asn Ser
505             510             515                     520

ATG GGC ACG TCT TGC GAA ACC ATC TTT TTA AAC TCA CCA GGC CCC TTC
Met Gly Thr Ser Cys Glu Thr Ile Phe Leu Asn Ser Pro Gly Pro Phe
                525             530                     535

CCT TTC ATC CAA GAC AAC ATC TCC TTC TAT GCG ACC ATT GGG CTC TGT
Pro Phe Ile Gln Asp Asn Ile Ser Phe Tyr Ala Thr Ile Gly Leu Cys
        540             545                     550

CTC CCC TTC ATT GTT GTT CTC ATT GTG TTG ATC TGC CAC AAA TAC AAA
Leu Pro Phe Ile Val Val Leu Ile Val Leu Ile Cys His Lys Tyr Lys
        555             560                     565

AAG CAA TTT AGG TAC GAG AGT CAG CTG CAG ATG ATC CAG GTG ACT GGC
Lys Gln Phe Arg Tyr Glu Ser Gln Leu Gln Met Ile Gln Val Thr Gly
570             575             580

CCC CTG GAT AAC GAG TAC TTC TAC GTT GAC TTC AGG GAC TAT GAA TAT
Pro Leu Asp Asn Glu Tyr Phe Tyr Val Asp Phe Arg Asp Tyr Glu Tyr
585             590             595             600

GAC CTT AAG TGG GAG TTC CCG AGA GAG AAC TTA GAG TTT GGG AAG GTC
Asp Leu Lys Trp Glu Phe Pro Arg Glu Asn Leu Glu Phe Gly Lys Val
                605             610                     615

CTG GGG TCT GGC GCT TTC GGG AGG GTG ATG AAC GCC ACG GCC TAT GGC
Leu Gly Ser Gly Ala Phe Gly Arg Val Met Asn Ala Thr Ala Tyr Gly
                620             625                     630

ATT AGT AAA ACG GGA GTC TCA ATT CAG GTG GCG GTG AAG ATG CTA AAA
Ile Ser Lys Thr Gly Val Ser Ile Gln Val Ala Val Lys Met Leu Lys
        635             640                     645

GAG AAA GCT GAC AGC TGT GAA AAA GAA GCT CTC ATG TCG GAG CTC AAA
Glu Lys Ala Asp Ser Cys Glu Lys Glu Ala Leu Met Ser Glu Leu Lys
650                 655                 660

ATG ATG ACC CAC CTG GGA CAC CAT GAC AAC ATC GTG AAT CTG CTG GGG
Met Met Thr His Leu Gly His His Asp Asn Ile Val Asn Leu Leu Gly
665                 670                 675                 680

GCA TGC ACA CTG TCA GGG CCA GTG TAC TTG ATT TTT GAA TAT TGT TGC
Ala Cys Thr Leu Ser Gly Pro Val Tyr Leu Ile Phe Glu Tyr Cys Cys
                685             690                     695

TAT GGT GAC CTC CTC AAC TAC CTA AGA AGT AAA AGA GAG AAG TTT CAC
Tyr Gly Asp Leu Leu Asn Tyr Leu Arg Ser Lys Arg Glu Lys Phe His
            700             705                     710
```

Figure 1d.

```
AGG ACA TGG ACA GAG ATT TTT AAG GAA CAT AAT TTC AGT TCT TAC CCT
Arg Thr Trp Thr Glu Ile Phe Lys Glu His Asn Phe Ser Ser Tyr Pro
        715             720             725

ACT TTC CAG GCA CAT TCA AAT TCC AGC ATG CCT GGT TCA CGA GAA GTT
Thr Phe Gln Ala His Ser Asn Ser Ser Met Pro Gly Ser Arg Glu Val
    730             735             740

CAG TTA CAC CCG CCC TTG GAT CAG CTC TCA GGG TTC AAT GGG AAT TCA
Gln Leu His Pro Pro Leu Asp Gln Leu Ser Gly Phe Asn Gly Asn Ser
745             750             755             760

ATT CAT TCT GAA GAT GAG ATT GAA TAT GAA AAC CAG AAG AGG CTG GCA
Ile His Ser Glu Asp Glu Ile Glu Tyr Glu Asn Gln Lys Arg Leu Ala
            765             770             775

GAA GAA GAG GAG GAA GAT TTG AAC GTG CTG ACG TTT GAA GAC CTC CTT
Glu Glu Glu Glu Glu Asp Leu Asn Val Leu Thr Phe Glu Asp Leu Leu
            780             785             790

TGC TTT GCG TAC CAA GTG GCC AAA GGC ATG GAA TTC CTG GAG TTC AAG
Cys Phe Ala Tyr Gln Val Ala Lys Gly Met Glu Phe Leu Glu Phe Lys
        795             800             805

TCG TGT GTC CAC AGA GAC CTG GCA GCC AGG AAT GTG TTG GTC ACC CAC
Ser Cys Val His Arg Asp Leu Ala Ala Arg Asn Val Leu Val Thr His
        810             815             820

GGG AAG GTG GTG AAG ATC TGT GAC TTT GGA CTG GCC CGA GAC ATC CTG
Gly Lys Val Val Lys Ile Cys Asp Phe Gly Leu Ala Arg Asp Ile Leu
825             830             835             840

AGC GAC TCC AGC TAC GTC GTC AGG GGC AAC GCA CGG CTG CCG GTG AAG
Ser Asp Ser Ser Tyr Val Val Arg Gly Asn Ala Arg Leu Pro Val Lys
            845             850             855

TGG ATG GCA CCC GAG AGC TTA TTT GAA GGG ATC TAC ACA ATC AAG AGT
Trp Met Ala Pro Glu Ser Leu Phe Glu Gly Ile Tyr Thr Ile Lys Ser
            860             865             870

GAC GTC TGG TCC TAC GGC ATC CTT CTC TGG GAG ATA TTT TCA CTG GGT
Asp Val Trp Ser Tyr Gly Ile Leu Leu Trp Glu Ile Phe Ser Leu Gly
        875             880             885

GTG AAC CCT TAC CCT GGC ATT CCT GTC GAC GCT AAC TTC TAT AAA CTG
Val Asn Pro Tyr Pro Gly Ile Pro Val Asp Ala Asn Phe Tyr Lys Leu
    890             895             900

ATT CAG AGT GGA TTT AAA ATG GAG CAG CCA TTC TAT GCC ACA GAA GGG
Ile Gln Ser Gly Phe Lys Met Glu Gln Pro Phe Tyr Ala Thr Glu Gly
905             910             915             920

ATA TAC TTT GTA ATG CAA TCC TGC TGG GCT TTT GAC TCA AGG AAG CGG
Ile Tyr Phe Val Met Gln Ser Cys Trp Ala Phe Asp Ser Arg Lys Arg
            925             930             935

CCA TCC TTC CCC AAC CTG ACT TCA TTT TTA GGA TGT CAG CTG GCA GAG
Pro Ser Phe Pro Asn Leu Thr Ser Phe Leu Gly Cys Gln Leu Ala Glu
        940             945             950
```

Figure 1e.

```
GCA GAA GAA GCA TGT ATC AGA ACA TCC ATC CAT CTA CCA AAA CAG GCG
Ala Glu Glu Ala Cys Ile Arg Thr Ser Ile His Leu Pro Lys Gln Ala
        955                 960                 965

GCC CCT CAG CAG AGA GGC GGG CTC AGA GCC CAG TCG CCA CAG CGC CAG
Ala Pro Gln Gln Arg Gly Gly Leu Arg Ala Gln Ser Pro Gln Arg Gln
    970                 975                 980

GTG AAG ATT CAC AGA GAA AGA AGT TAGCGAGGAG GCCTTGGACC CCGCCACCCT
Val Lys Ile His Arg Glu Arg Ser
985                 990
```

```
AGCAGGCTGT AGACCGCAGA GCCAAGATTA GCCTCGCCTC TGAGGAAGCG CCCTACAGCG

CGTTGCTTCG CTGGACTTTT CTCTAGATGC TGTCTGCCAT TACTCCAAAG TGACTTCTAT

AAAATCAAAC CTCTCCTCGC ACAGGCGGGA GAGCCAATAA TGAGACTTGT TGGTGAGCCC

GCCTACCCTG GGGGCCTTTC CACGAGCTTG AGGGGAAAGC CATGTATCTG AAATATAGTA

TATTCTTGTA AATACGTGAA ACAAACCAAA CCCGTTTTTT GCTAAGGGAA AGCTAAATAT

GATTTTTAAA AATCTATGTT TTAAAATACT ATGTAACTTT TTCATCTATT TAGTGATATA

TTTTATGGAT GGAAATAAAC TTTCTACTGT AAAAAAAAAA AAAAAAAAAA AAAAAA
```

Figure 2a.

CTGTGTCCCG CAGCCGGATA ACCTGGCTGA CCCGATTCCG CGGACACCCG TGCAGCCGCG

GCTGGAGCCA GGGCGCCGGT GCCCGCGCTC TCCCCGGTCT TGCGCTGCGG GGGCCGATAC

CGCCTCTGTG ACTTCTTTGC GGGCCAGGGA CGGAGAAGGA GTCTGTGCCT GAGAAACTGG

GCTCTGTGCC CAGGCGCGAG GTGCAGG ATG GAG AGC AAG GGC CTG CTA GCT
                                                          Met Glu Ser Lys Gly Leu Leu Ala
                                                           1                5

GTC GCT CTG TGG TTC TGC GTG GAG ACC CGA GCC GCC TCT GTG GGT TTG
Val Ala Leu Trp Phe Cys Val Glu Thr Arg Ala Ala Ser Val Gly Leu
    10                    15                    20

CCT GGC GAT TTT CTC CAT CCC CCC AAG CTC AGC ACA CAG AAA GAC ATA
Pro Gly Asp Phe Leu His Pro Pro Lys Leu Ser Thr Gln Lys Asp Ile
25                    30                    35                    40

CTG ACA ATT TTG GCA AAT ACA ACC CTT CAG ATT ACT TGC AGG GGA CAG
Leu Thr Ile Leu Ala Asn Thr Thr Leu Gln Ile Thr Cys Arg Gly Gln
                45                    50                    55

CGG GAC CTG GAC TGG CTT TGG CCC AAT GCT CAG CGT GAT TCT GAG GAA
Arg Asp Leu Asp Trp Leu Trp Pro Asn Ala Gln Arg Asp Ser Glu Glu
            60                    65                    70

AGG GTA TTG GTG ACT GAA TGC GGC GGT GGT GAC AGT ATC TTC TGC AAA
Arg Val Leu Val Thr Glu Cys Gly Gly Gly Asp Ser Ile Phe Cys Lys
          75                    80                    85

ACA CTC ACC ATT CCC AGG GTG GTT GGA AAT GAT ACT GGA GCC TAC AAG
Thr Leu Thr Ile Pro Arg Val Val Gly Asn Asp Thr Gly Ala Tyr Lys
          90                    95                  100

TGC TCG TAC CGG GAC GTC GAC ATA GCC TCC ACT GTT TAT GTC TAT GTT
Cys Ser Tyr Arg Asp Val Asp Ile Ala Ser Thr Val Tyr Val Tyr Val
105                  110                  115                120

CGA GAT TAC AGA TCA CCA TTC ATC GCC TCT GTC AGT GAC CAG CAT GGC
Arg Asp Tyr Arg Ser Pro Phe Ile Ala Ser Val Ser Asp Gln His Gly
                125                  130                135

ATC GTG TAC ATC ACC GAG AAC AAG AAC AAA ACT GTG GTG ATC CCC TGC
Ile Val Tyr Ile Thr Glu Asn Lys Asn Lys Thr Val Val Ile Pro Cys
            140                    145                  150

CGA GGG TCG ATT TCA AAC CTC AAT GTG TCT CTT TGC GCT AGG TAT CCA
Arg Gly Ser Ile Ser Asn Leu Asn Val Ser Leu Cys Ala Arg Tyr Pro
          155                    160                  165

GAA AAG AGA TTT GTT CCG GAT GGA AAC AGA ATT TCC TGG GAC AGC GAG
Glu Lys Arg Phe Val Pro Asp Gly Asn Arg Ile Ser Trp Asp Ser Glu
     170                    175                  180

ATA GGC TTT ACT CTC CCC AGT TAC ATG ATC AGC TAT GCC GGC ATG GTC
Ile Gly Phe Thr Leu Pro Ser Tyr Met Ile Ser Tyr Ala Gly Met Val
185                  190                  195                200

Figure 2b.

| | | | | | | | | | | | | | | |
|---|---|---|---|---|---|---|---|---|---|---|---|---|---|---|
| TTC | TGT | GAG | GCA | AAG | ATC | AAT | GAT | GAA | ACC | TAT | CAG | TCT | ATC | ATG | TAC |
| Phe | Cys | Glu | Ala | Lys | Ile | Asn | Asp | Glu | Thr | Tyr | Gln | Ser | Ile | Met | Tyr |
| | | | 205 | | | | 210 | | | | | 215 | | | |

```
TTC TGT GAG GCA AAG ATC AAT GAT GAA ACC TAT CAG TCT ATC ATG TAC
Phe Cys Glu Ala Lys Ile Asn Asp Glu Thr Tyr Gln Ser Ile Met Tyr
             205             210              215

ATA GTT GTG GTT GTA GGA TAT AGG ATT TAT GAT GTG ATT CTG AGC CCC
Ile Val Val Val Val Gly Tyr Arg Ile Tyr Asp Val Ile Leu Ser Pro
             220             225              230

CCG CAT GAA ATT GAG CTA TCT GCC GGA GAA AAA CTT GTC TTA AAT TGT
Pro His Glu Ile Glu Leu Ser Ala Gly Glu Lys Leu Val Leu Asn Cys
             235             240              245

ACA GCG AGA ACA GAG CTC AAT GTG GGG CTT GAT TTC ACC TGG CAC TCT
Thr Ala Arg Thr Glu Leu Asn Val Gly Leu Asp Phe Thr Trp His Ser
             250             255              260

CCA CCT TCA AAG TCT CAT CAT AAG AAG ATT GTA AAC CGG GAT GTG AAA
Pro Pro Ser Lys Ser His His Lys Lys Ile Val Asn Arg Asp Val Lys
265              270             275              280

CCC TTT CCT GGG ACT GTG GCG AAG ATG TTT TTG AGC ACC TTG ACA ATA
Pro Phe Pro Gly Thr Val Ala Lys Met Phe Leu Ser Thr Leu Thr Ile
             285             290              295

GAA AGT GTG ACC AAG AGT GAC CAA GGG GAA TAC ACC TGT GTA GCG TCC
Glu Ser Val Thr Lys Ser Asp Gln Gly Glu Tyr Thr Cys Val Ala Ser
             300             305              310

AGT GGA CGG ATG ATC AAG AGA AAT AGA ACA TTT GTC CGA GTT CAC ACA
Ser Gly Arg Met Ile Lys Arg Asn Arg Thr Phe Val Arg Val His Thr
             315             320              325

AAG CCT TTT ATT GCT TTC GGT AGT GGG ATG AAA TCT TTG GTG GAA GCC
Lys Pro Phe Ile Ala Phe Gly Ser Gly Met Lys Ser Leu Val Glu Ala
     330             335             340

ACA GTG GGC AGT CAA GTC CGA ATC CCT GTG AAG TAT CTC AGT TAC CCA
Thr Val Gly Ser Gln Val Arg Ile Pro Val Lys Tyr Leu Ser Tyr Pro
345              350             355              360

GCT CCT GAT ATC AAA TGG TAC AGA AAT GGA AGG CCC ATT GAG TCC AAC
Ala Pro Asp Ile Lys Trp Tyr Arg Asn Gly Arg Pro Ile Glu Ser Asn
             365             370              375

TAC ACA ATG ATT GTT GGC GAT GAA CTC ACC ATC ATG GAA GTG ACT GAA
Tyr Thr Met Ile Val Gly Asp Glu Leu Thr Ile Met Glu Val Thr Glu
             380             385              390

AGA GAT GCA GGA AAC TAC ACG GTC ATC CTC ACC AAC CCC ATT TCA ATG
Arg Asp Ala Gly Asn Tyr Thr Val Ile Leu Thr Asn Pro Ile Ser Met
             395             400              405

GAG AAA CAG AGC CAC ATG GTC TCT CTG GTT GTG AAT GTC CCA CCC CAG
Glu Lys Gln Ser His Met Val Ser Leu Val Val Asn Val Pro Pro Gln
     410             415             420

ATC GGT GAG AAA GCC TTG ATC TCG CCT ATG GAT TCC TAC CAG TAT GGG
Ile Gly Glu Lys Ala Leu Ile Ser Pro Met Asp Ser Tyr Gln Tyr Gly
425              430             435              440
```

Figure 2c.

| | | | | | | | | | | | | |
|---|---|---|---|---|---|---|---|---|---|---|---|---|
| ACC | ATG | CAG | ACA | TTG | ACA | TGC | ACA | GTC | TAC | GCC | AAC | CCT | CCC | CTG | CAC |
| Thr | Met | Gln | Thr | Leu | Thr | Cys | Thr | Val | Tyr | Ala | Asn | Pro | Pro | Leu | His |
| | | | 445 | | | | | 450 | | | | | | 455 | |

```
ACC ATG CAG ACA TTG ACA TGC ACA GTC TAC GCC AAC CCT CCC CTG CAC
Thr Met Gln Thr Leu Thr Cys Thr Val Tyr Ala Asn Pro Pro Leu His
            445             450                     455

CAC ATC CAG TGG TAC TGG CAG CTA GAA GAA GCC TGC TCC TAC AGA CCC
His Ile Gln Trp Tyr Trp Gln Leu Glu Glu Ala Cys Ser Tyr Arg Pro
            460             465                     470

GGC CAA ACA AGC CCG TAT GCT TGT AAA GAA TGG AGA CAC GTG GAG GAT
Gly Gln Thr Ser Pro Tyr Ala Cys Lys Glu Trp Arg His Val Glu Asp
            475             480                     485

TTC CAG GGG GGA AAC AAG ATC GAA GTC ACC AAA AAC CAA TAT GCC CTG
Phe Gln Gly Gly Asn Lys Ile Glu Val Thr Lys Asn Gln Tyr Ala Leu
            490             495                     500

ATT GAA GGA AAA AAC AAA ACT GTA AGT ACG CTG GTC ATC CAA GCT GCC
Ile Glu Gly Lys Asn Lys Thr Val Ser Thr Leu Val Ile Gln Ala Ala
505             510             515                     520

AAC GTG TCA GCG TTG TAC AAA TGT GAA GCC ATC AAC AAA GCG GGA CGA
Asn Val Ser Ala Leu Tyr Lys Cys Glu Ala Ile Asn Lys Ala Gly Arg
            525             530                     535

GGA GAG AGG GTC ATC TCC TTC CAT GTG ATC AGG GGT CCT GAA ATT ACT
Gly Glu Arg Val Ile Ser Phe His Val Ile Arg Gly Pro Glu Ile Thr
            540             545                     550

GTG CAA CCT GCT GCC CAG CCA ACT GAG CAG GAG AGT GTG TCC CTG TTG
Val Gln Pro Ala Ala Gln Pro Thr Glu Gln Glu Ser Val Ser Leu Leu
            555             560                     565

TGC ACT GCA GAC AGA AAT ACG TTT GAG AAC CTC ACG TGG TAC AAG CTT
Cys Thr Ala Asp Arg Asn Thr Phe Glu Asn Leu Thr Trp Tyr Lys Leu
            570             575                     580

GGC TCA CAG GCA ACA TCG GTC CAC ATG GGC GAA TCA CTC ACA CCA GTT
Gly Ser Gln Ala Thr Ser Val His Met Gly Glu Ser Leu Thr Pro Val
585             590             595                     600

TGC AAG AAC TTG GAT GCT CTT TGG AAA CTG AAT GGC ACC ATG TTT TCT
Cys Lys Asn Leu Asp Ala Leu Trp Lys Leu Asn Gly Thr Met Phe Ser
            605             610                     615

AAC AGC ACA AAT GAC ATC TTG ATT GTG GCA TTT CAG AAT GCC TCT CTG
Asn Ser Thr Asn Asp Ile Leu Ile Val Ala Phe Gln Asn Ala Ser Leu
            620             625                     630

CAG GAC CAA GGC GAC TAT GTT TGC TCT GCT CAA GAT AAG AAG ACC AAG
Gln Asp Gln Gly Asp Tyr Val Cys Ser Ala Gln Asp Lys Lys Thr Lys
            635             640                     645

AAA AGA CAT TGC CTG GTC AAA CAG CTC ATC ATC CTA GAG CGC ATG GCA
Lys Arg His Cys Leu Val Lys Gln Leu Ile Ile Leu Glu Arg Met Ala
            650             655                     660

CCC ATG ATC ACC GGA AAT CTG GAG AAT CAG ACA ACA ACC ATT GGC GAG
Pro Met Ile Thr Gly Asn Leu Glu Asn Gln Thr Thr Thr Ile Gly Glu
665             670             675                     680
```

Figure 2d.

```
ACC ATT GAA GTG ACT TGC CCA GCA TCT GGA AAT CCT ACC CCA CAC ATT
Thr Ile Glu Val Thr Cys Pro Ala Ser Gly Asn Pro Thr Pro His Ile
            685             690                 695

ACA TGG TTC AAA GAC AAC GAG ACC CTG GTA GAA GAT TCA GGC ATT GTA
Thr Trp Phe Lys Asp Asn Glu Thr Leu Val Glu Asp Ser Gly Ile Val
            700             705                 710

CTG AGA GAT GGG AAC CGG AAC CTG ACT ATC CGC AGG GTG AGG AAG GAG
Leu Arg Asp Gly Asn Arg Asn Leu Thr Ile Arg Arg Val Arg Lys Glu
            715             720                 725

GAT GGA GGC CTC TAC ACC TGC CAG GCC TGC AAT GTC CTT GGC TGT GCA
Asp Gly Gly Leu Tyr Thr Cys Gln Ala Cys Asn Val Leu Gly Cys Ala
            730             735                 740

AGA GCG GAG ACG CTC TTC ATA ATA GAA GGT GCC CAG GAA AAG ACC AAC
Arg Ala Glu Thr Leu Phe Ile Ile Glu Gly Ala Gln Glu Lys Thr Asn
745             750             755                 760

TTG GAA GTC ATT ATC CTC GTC GGC ACT GCA GTG ATT GCC ATG TTC TTC
2Leu Glu Val Ile Ile Leu Val Gly Thr Ala Val Ile Ala Met Phe Phe
            765             770                 775

TGG CTC CTT CTT GTC ATT CTC GTA CGG ACC GTT AAG CGG GCC AAT GAA
Trp Leu Leu Leu Val Ile Leu Val Arg Thr Val Lys Arg Ala Asn Glu
            780             785                 790

GGG GAA CTG AAG ACA GGC TAC TTG TCT ATT GTC ATG GAT CCA GAT GAA
Gly Glu Leu Lys Thr Gly Tyr Leu Ser Ile Val Met Asp Pro Asp Glu
            795             800                 805

TTG CCC TTG GAT GAG CGC TGT GAA CGC TTG CCT TAT GAT GCC AGC AAG
Leu Pro Leu Asp Glu Arg Cys Glu Arg Leu Pro Tyr Asp Ala Ser Lys
            810             815                 820

TGG GAA TTC CCC AGG GAC CGG CTG AAA CTA GGA AAA CCT CTT GGC CGC
Trp Glu Phe Pro Arg Asp Arg Leu Lys Leu Gly Lys Pro Leu Gly Arg
825             830             835                 840

GGT GCC TTC GGC CAA GTG ATT GAG GCA GAC GCT TTT GGA ATT GAC AAG
Gly Ala Phe Gly Gln Val Ile Glu Ala Asp Ala Phe Gly Ile Asp Lys
            845             850                 855

ACA GCG ACT TGC AAA ACA GTA GCC GTC AAG ATG TTG AAA GAA GGA GCA
Thr Ala Thr Cys Lys Thr Val Ala Val Lys Met Leu Lys Glu Gly Ala
            860             865                 870

ACA CAC AGC GAG CAT CGA GCC CTC ATG TCT GAA CTC AAG ATC CTC ATC
Thr His Ser Glu His Arg Ala Leu Met Ser Glu Leu Lys Ile Leu Ile
            875             880                 885

CAC ATT GGT CAC CAT CTC AAT GTG GTG AAC CTC TA GGC GCC TGC ACC
His Ile Gly His His Leu Asn Val Val Asn Leu Leu Gly Ala Cys Thr
    890             895                 900

AAG CCG GGA GGG CCT CTC ATG GTG ATT GTG GAA TTC TCG AAG TTT GGA
Lys Pro Gly Gly Pro Leu Met Val Ile Val Glu Phe Ser Lys Phe Gly
905             910             915                 920
```

Figure 2e.

```
AAC CTA TCA ACT TAC TTA CGG GGC AAG AGA AAT GAA TTT GTT CCC TAT
Asn Leu Ser Thr Tyr Leu Arg Gly Lys Arg Asn Glu Phe Val Pro Tyr
            925             930                 935

AAG AGC AAA GGG GCA CGC TTC CGC CAG GGC AAG GAC TAC GTT GGG GAG
Lys Ser Lys Gly Ala Arg Phe Arg Gln Gly Lys Asp Tyr Val Gly Glu
            940             945                 950

CTC TCC GTG GAT CTG AAA AGA CGC TTG GAC AGC ATC ACC AGC AGC CAG
Leu Ser Val Asp Leu Lys Arg Arg Leu Asp Ser Ile Thr Ser Ser Gln
            955             960                 965

AGC TCT GCC AGC TCA GGC TTT GTT GAG GAG AAA TCG CTC AGT GAT GTA
Ser Ser Ala Ser Ser Gly Phe Val Glu Glu Lys Ser Leu Ser Asp Val
    970             975                 980

GAG GAA GAA GAA GCT TCT GAA GAA CTG TAC AAG GAC TTC CTG ACC TTG
Glu Glu Glu Glu Ala Ser Glu Glu Leu Tyr Lys Asp Phe Leu Thr Leu
985             990             995                         1000

GAG CAT CTC ATC TGT TAC AGC TTC CAA GTG GCT AAG GGC ATG GAG TTC
Glu His Leu Ile Cys Tyr Ser Phe Gln Val Ala Lys Gly Met Glu Phe
                1005            1010                1015

TTG GCA TCA AGG AAG TGT ATC CAC AGG GAC CTG GCA GCA CGA AAC ATT
Leu Ala Ser Arg Lys Cys Ile His Arg Asp Leu Ala Ala Arg Asn Ile
            1020            1025                1030

CTC CTA TCG GAG AAG AAT GTG GTT AAG ATC TGT GAC TTC GGC TTG GCC
Leu Leu Ser Glu Lys Asn Val Val Lys Ile Cys Asp Phe Gly Leu Ala
            1035            1040                1045

CGG GAC ATT TAT AAA GAC CCG GAT TAT GTC AGA AAA GGA GAT GCC CGA
Arg Asp Ile Tyr Lys Asp Pro Asp Tyr Val Arg Lys Gly Asp Ala Arg
            1050            1055                1060

CTC CCT TTG AAG TGG ATG GCC CCG GAA ACC ATT TTT GAC AGA GTA TAC
Leu Pro Leu Lys Trp Met Ala Pro Glu Thr Ile Phe Asp Arg Val Tyr
1065            1070            1075                        1080

ACA ATT CAG AGC GAT GTG TGG TCT TTC GGT GTG TTG CTC TGG GAA ATA
Thr Ile Gln Ser Asp Val Trp Ser Phe Gly Val Leu Leu Trp Glu Ile
            1085            1090                1095

TTT TCC TTA GGT GCC TCC CCA TAC CCT GGG GTC AAG ATT GAT GAA GAA
Phe Ser Leu Gly Ala Ser Pro Tyr Pro Gly Val Lys Ile Asp Glu Glu
            1100            1105                1110

TTT TGT AGG AGA TTG AAA GAA GGA ACT AGA ATG CGG GCT CCT GAC TAC
Phe Cys Arg Arg Leu Lys Glu Gly Thr Arg Met Arg Ala Pro Asp Tyr
            1115            1120                1125

ACT ACC CCA GAA ATG TAC CAG ACC ATG CTG GAC TGC TGG CAT GAG GAC
Thr Thr Pro Glu Met Tyr Gln Thr Met Leu Asp Cys Trp His Glu Asp
1130            1135                1140

CCC AAC CAG AGA CCC TCG TTT TCA GAG TTG GTG GAG CAT TTG GGA AAC
Pro Asn Gln Arg Pro Ser Phe Ser Glu Leu Val Glu His Leu Gly Asn
1145            1150            1155                        1160
```

Figure 2f.

```
CTC CTG CAA GCA AAT GCG CAG CAG GAT GGC AAA GAC TAT ATT GTT CTT
Leu Leu Gln Ala Asn Ala Gln Gln Asp Gly Lys Asp Tyr Ile Val Leu
            1165            1170            1175

CCA ATG TCA GAG ACA CTG AGC ATG GAA GAG GAT TCT GGA CTC TCC CTG
Pro Met Ser Glu Thr Leu Ser Met Glu Glu Asp Ser Gly Leu Ser Leu
            1180            1185            1190

CCT ACC TCA CCT GTT TCC TGT ATG GAG GAA GAG GAA GTG TGC GAC CCC
Pro Thr Ser Pro Val Ser Cys Met Glu Glu Glu Glu Val Cys Asp Pro
            1195            1200            1205

AAA TTC CAT TAT GAC AAC ACA GCA GGA ATC AGT CAT TAT CTC CAG AAC
Lys Phe His Tyr Asp Asn Thr Ala Gly Ile Ser His Tyr Leu Gln Asn
            1210            1215            1220

AGT AAG CGA AAG AGC CGG CCA GTG AGT GTA AAA ACA TTT GAA GAT ATC
Ser Lys Arg Lys Ser Arg Pro Val Ser Val Lys Thr Phe Glu Asp Ile
1225            1230            1235            1240

CCA TTG GAG GAA CCA GAA GTA AAA GTG ATC CCA GAT GAC AGC CAG ACA
Pro Leu Glu Glu Pro Glu Val Lys Val Ile Pro Asp Asp Ser Gln Thr
            1245            1250            1255

GAC AGT GGG ATG GTC CTT GCA TCA GAA GAG CTG AAA ACT CTG GAA GAC
Asp Ser Gly Met Val Leu Ala Ser Glu Glu Leu Lys Thr Leu Glu Asp
            1260            1265            1270

AGG AAC AAA TTA TCT CCA TCT TTT GGT GGA ATG ATG CCC AGT AAA AGC
Arg Asn Lys Leu Ser Pro Ser Phe Gly Gly Met Met Pro Ser Lys Ser
            1275            1280            1285

AGG GAG TCT GTG GCC TCG GAA GGC TCC AAC CAG ACC AGT GGC TAC CAG
Arg Glu Ser Val Ala Ser Glu Gly Ser Asn Gln Thr Ser Gly Tyr Gln
            1290            1295            1300

TCT GGG TAT CAC TCA GAT GAC ACA GAC ACC ACC GTG TAC TCC AGC GAC
Ser Gly Tyr His Ser Asp Asp Thr Asp Thr Thr Val Tyr Ser Ser Asp
1305            1310            1315            1320

GAG GCA GGA CTT TTA AAG ATG GTG GAT GCT GCA GTT CAC GCT GAC TCA
Glu Ala Gly Leu Leu Lys Met Val Asp Ala Ala Val His Ala Asp Ser
            1325            1330            1335

GGG ACC ACA CTG CAG CTC ACC TCC TGT TTA AAT GGA AGT GGT CCT GTC
Gly Thr Thr Leu Gln Leu Thr Ser Cys Leu Asn Gly Ser Gly Pro Val
            1340            1345            1350

CCG GCT CCG CCC CCA ACT CCT GGA AAT CAC GAG AGA GGT GCT GCT TAG
Pro Ala Pro Pro Pro Thr Pro Gly Asn His Glu Arg Gly Ala Ala
            1355            1360            1365

ATTTTCAAGT GTTGTTCTTT CCACCACCCG GAAGTAGCCA CATTTGATTT TCATTTTTGG

AGGAGGGACC TCAGACTGCA AGGAGCTTGT CCTCAGGGCA TTTCCAGAGA AGATGCCCAT

GACCCAAGAA TGTGTTGACT CTACTCTCTT TTCCATTCAT TTAAAAGTCC TATATAATGT
```

Figure 2g.

```
GCCCTGCTGT GGTCTCACTA CCAGTTAAAG CAAAAGACTT TCAAACACGT GGACTCTGTC
CTCCAAGAAG TGGCAACGGC ACCTCTGTGA AACTGGATCG AATGGGCAAT GCTTTGTGTG
TTGAGGATGG GTGAGATGTC CCAGGGCCGA GTCTGTCTAC CTTGGAGGCT TTGTGGAGGA
TGCGGCTATG AGCCAAGTGT TAAGTGTGGG ATGTGGACTG GGAGGAAGGA AGGCGCAAGC
CGTCCGGAGA GCGGTTGGAG CCTGCAGATG CATTGTGCTG GCTCTGGTGG AGGTGGGCTT
GTGGCCTGTC AGGAAACGCA AAGGCGGCCG GCAGGGTTTG GTTTTGGAAG GTTTGCGTGC
TCTTCACAGT CGGGTTACAG GCGAGTTCCC TGTGGCGTTT CCTACTCCTA ATGAGAGTTC
CTTCCGGACT CTTACGTGTC TCCTGGCCTG GCCCCAGGAA GGAAATGATG CAGCTTGCTC
CTTCCTCATC TCTCAGGCTG TGCCTTAATT CAGAACACCA AAAGAGAGGA ACGTCGGCAG
AGGCTCCTGA CGGGGCCGAA GAATTGTGAG AACAGAACAG AAACTCAGGG TTTCTGCTGG
GTGGAGACCC ACGTGGCGCC CTGGTGGCAG GTCTGAGGGT TCTCTGTCAA GTGGCGGTAA
AGGCTCAGGC TGGTGTTCTT CCTCTATCTC CACTCCTGTC AGGCCCCCAA GTCCTCAGTA
TTTTAGCTTT GTGGCTTCCT GATGGCAGAA AAATCTTAAT TGGTTGGTTT GCTCTCCAGA
TAATCACTAG CCAGATTTCG AAATTACTTT TTAGCCGAGG TTATGATAAC ATCTACTGTA
TCCTTTAGAA TTTTAACCTA TAAAACTATG TCTACTGGTT TCTGCCTGTG TGCTTATGTT
AAAAAAAAAA AAAAA
```

NUCLEIC ACIDS ENCODING HEMATOPOIETIC STEM CELLS RECEPTORS FLK-1

The invention described in this application was made with U.S. government support from Grant Numbers R01-CA45339 and R01-DK42989 awarded by the National Institutes of Health. The government has certain rights in this invention.

This is a continuation of copending application(s) Ser. No. 07/813,593 filed on Dec. 24, 1991, issued as U.S. Pat No. 5,185,438, which is a continuation-in-part of Ser. No. 793,065 filed Nov. 15, 1991, which is a continuation-in-part of Ser. No. 728,913 filed Jun. 28, 1991 now abandoned, which is a continuation-in-part of Ser. No. 679,666 filed Apr. 2, 1991 now abandoned, all of which are incorporated herein by reference.

FIELD OF THE INVENTION

The present invention relates to hematopoietic stem cell receptors, ligands for such receptors, and nucleic acid molecules encoding such receptors and ligands.

BACKGROUND OF THE INVENTION

The mammalian hematopoietic system comprises red and white blood cells. These cells are the mature cells that result from more primitive lineage-restricted cells. The cells of the hematopoietic system have been reviewed by Dexter and Spooncer in the Annual Review of Cell Biology 3, 423–441 (1987).

The red blood cells, or erythrocytes, result from primitive cells referred to by Dexter and Spooncer as erythroid burst-forming units (BFU-E). The immediate progeny of the erythroid burst-forming units are called erythroid colony-forming units (CFU-E).

The white blood cells contain the mature cells of the lymphoid and myeloid systems. The lymphoid cells include B-lymphocytes and T lymphocytes. The B and T lymphocytes result from earlier progenitor cells referred to by Dexter and Spooncer as preT and preB cells.

The myeloid system comprises a number of cells including granulocytes, platelets, monocytes, macrophages, and megakaryocytes. The granulocytes are further divided into neutrophils, eosinophils, basophils and mast cells.

Each of the mature hematopoietic cells are specialized for specific functions. For example, erythrocytes are responsible for oxygen and carbon dioxide transport. T and B lymphocytes are responsible for cell- and antibody-mediated immune responses, respectively. Platelets are involved in blood clotting. Granulocytes and macrophages act generally as scavengers and accessory cells in the immune response against invading organisms and their by-products.

At the center of the hematopoietic system lie one or more totipotent hematopoietic stem cells, which undergo a series of differentiation steps leading to increasingly lineage-restricted progenitor cells. The more mature progenitor cells are restricted to producing one or two lineages. Some examples of lineage-restricted progenitor cells mentioned by Dexter and Spooncer include granulocyte/macrophage colony-forming cells (GM-CFC), megakaryocyte colony-forming cells (Meg-CFC), eosinophil colony-forming cells (Eos-CFC), and basophil colony-forming cells (Bas-CFC). Other examples of progenitor cells are discussed above.

The hematopoietic system functions by means of a precisely controlled production of the various mature lineages. The totipotent stem cell possesses the ability both to self renew and to differentiate into committed progenitors for all hematopoietic lineages. These most primitive of hematopoietic cells are both necessary and sufficient for the complete and permanent hematopoietic reconstitution of a radiation-ablated hematopoietic system in mammals. The ability of stem cells to reconstitute the entire hematopoietic system is the basis of bone marrow transplant therapy.

It is known that growth factors play an important role in the development and operation of the mammalian hematopoietic system. The role of growth factors is complex, however, and not well understood at the present time. One reason for the uncertainty is that much of what is known about hematopoietic growth factors results from in vitro experiments. Such experiments do not necessarily reflect in vivo realities.

In addition, in vitro hematopoiesis can be established in the absence of added growth factors, provided that marrow stromal cells are added to the medium. The relationship between stromal cells and hematopoietic growth factors in vivo is not understood. Nevertheless, hematopoietic growth factors have been shown to be highly active in vivo.

From what is known about them, hematopoietic growth factors appear to exhibit a spectrum of activities. At one end of the spectrum are growth factors such as erythropoietin, which is believed to promote proliferation only of mature erythroid progenitor cells. In the middle of the spectrum are growth factors such as IL-3, which is believed to facilitate the growth and development of early stem cells as well as of numerous progenitor cells. Some examples of progenitor cells induced by IL-3 include those restricted to the granulocyte/macrophage, eosinophil, megakaryocyte, erythroid and mast cell lineages.

At the other end of the spectrum is the hematopoietic growth factor that, along with the corresponding receptor, was discussed in a series of articles in the Oct. 5, 1990 edition of Cell. The receptor is the product of the W locus, c-kit, which is a member of the class of receptor protein tyrosine kinases. The ligand for c-kit, which is referred to by various names such as stem cell factor (SCF) and mast cell growth factor (MGF), is believed to be essential for the development of early hematopoietic stem cells and cells restricted to the erythroid and mast cell lineages in mice; see, for example, Copeland et al., Cell 63, 175–183 (1990).

It appears, therefore, that there are growth factors that exclusively affect mature cells. There also appear to be growth factors that affect both mature cells and stem cells. The growth factors that affect both types of cells may affect a small number or a large number of mature cells.

There further appears to be an inverse relationship between the ability of a growth factor to affect mature cells and the ability of the growth factor to affect stem cells. For example, the c-kit ligand, which stimulates a small number of mature cells, is believed to be more important in the renewal and development of stem cells then is IL-3, which is reported to stimulate proliferation of many mature cells (see above).

Prior to the present specification, there have been no reports of growth factors that exclusively stimulate stem cells in the absence of an effect on mature cells.

The discovery of such growth factors would be of particular significance.

As mentioned above, c-kit is a protein tyrosine kinase (pTK). It is becoming increasingly apparent that the protein tyrosine kinases play an important role as cellular receptors for hematopoietic growth factors. Other receptor pTKs include the receptors of colony stimulating factor 1(CSF-1) and PDGF.

The pTK family can be recognized by the presence of several conserved amino acid regions in the catalytic domain. These conserved regions are summarized by Hanks et al. in Science 241, 42-52 (1988), see FIG. 1 starting on page 46 and by Wilks in Proc. Natl. Acad. Sci. USA 86, 1603-1607 (1989), see FIG. 2 on page 1605.

Additional protein tyrosine kinases that represent hematopoietic growth factor receptors are needed in order more effectively to stimulate the self-renewal of the totipotent hematopoietic stem cell and to stimulate the development of all cells of the hematopoietic system both in vitro and in vivo. Novel hematopoietic growth factor receptors that are present only on primitive stem cells, but are not present on mature progenitor cells, are particularly desired. Ligands for the novel receptors are also desirable to act as hematopoietic growth factors. Nucleic acid sequences encoding the receptors and ligands are needed to produce recombinant receptors and ligands.

SUMMARY OF THE INVENTION

These and other objectives as will be apparent to those with ordinary skill in the art have been met by providing isolated mammalian nucleic acid molecules encoding receptor protein tyrosine kinases expressed in primitive hematopoietic cells and not expressed in mature hematopoietic cells. Also included are the receptors encoded by such nucleic acid molecules; the nucleic acid molecules encoding receptor protein tyrosine kinases having the sequences shown in FIG. 1 (flk-2, SEQIDNO:1 and 2) and FIG. 2 (flk-1, SEQIDNO:3 and 4); the receptor protein tyrosine kinases having the amino acid sequences shown in FIG. 1 (flk-2) and FIG. 2 (flk-1); ligands for the receptors; nucleic acid sequences that encode the ligands; and methods of stimulating the proliferation of primitive mammalian hematopoietic stem cells comprising contacting the stem cells with a ligand that binds to a receptor protein tyrosine kinase expressed in primitive mammalian hematopoietic cells and not expressed in mature hematopoietic cells.

DESCRIPTION OF THE FIGURES

FIG. 1a through FIG. 1E shows the cDNA and amino acid sequences of flk-2(SEQ ID NO:1 and 2). The amino acid residues occur directly below the nucleotides in the open reading frame. Amino acids 1-27 constitute the hydrophobic leader sequence. Amino acids 28-544 constitute the extracellular receptor domain. Amino acids 545-564 constitute the transmembrane region. The remainder of the amino acids constitute the intracellular catalytic domain. The following amino acid residues in the intracellular domain are catalytic sub-domains identified by Hanks (see above): 545-564, 618-623, 811-819, 832-834, 857-862, 872-878. The sequence at residues 709-785 is a signature sequence characteristic of flk-2. The protein tyrosine kinases generally have a signature sequence in this region. For the purposes of this specification and the claims, it is understood that all references to FIG. 1 includes FIGS. 1a through 1e.

FIG. 2a through FIGS. 2g shows the cDNA and amino acid sequences of flk-1 (SEQ ID NO:3 and 4). Amino acid residue 763-784 constitute the transmembrane region of flk-1. For the purposes of this specification and the claims, it is understood that all references to FIG. 2 includes FIGS. 2a through 2g.

DETAILED DESCRIPTION OF THE INVENTION

Receptors

Figure 3:
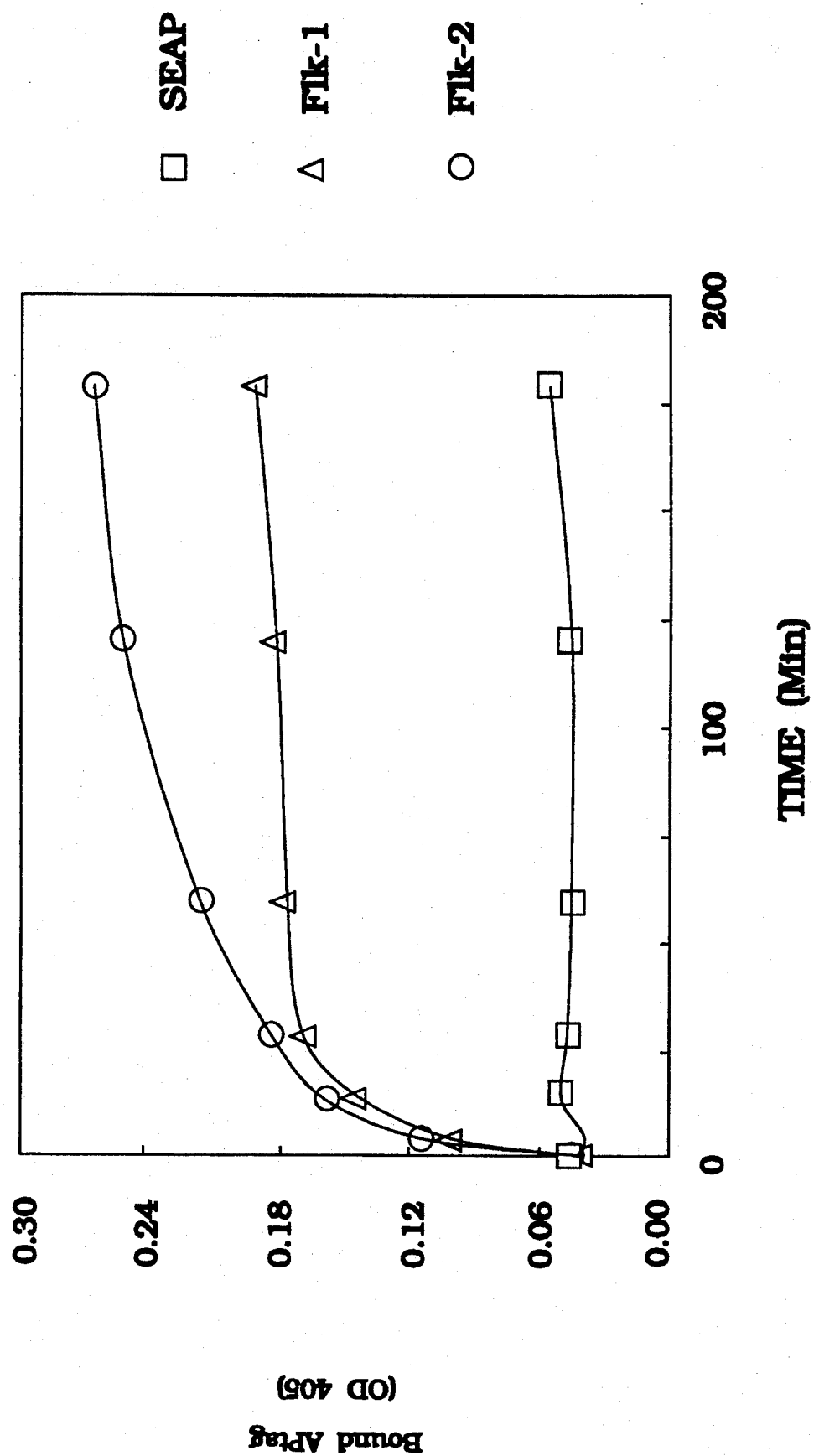
FIG. 3 shows the time response of binding between stromal cells (2018) and APtag-flk-2 as well as APtag-flk-1. APtag without receptor (SEAP) is used as a control. See Example 8.

In one embodiment, the invention relates to an isolated mammalian nucleic acid molecule encoding a receptor protein tyrosine kinase expressed in primitive mammalian hematopoietic cells and not expressed in mature hematopoietic cells.

The nucleic acid molecule may be a DNA, cDNA, or RNA molecule. The mammal in which the nucleic acid molecule exists may be any mammal, such as a mouse, rat, rabbit, or human.

The nucleic acid molecule encodes a protein tyrosine kinase (pTK). Members of the pTK family can be recognized by the conserved amino acid regions in the catalytic domains. Examples of pTK consensus sequences have been provided by Hanks et al. in Science 241, 42-52 (1988); see especially FIG. 1 starting on page 46 and by Wilks in Proc. Natl. Acad. Sci. USA 86, 1603-1607 (1989); see especially FIG. 2 on page 1605. A methionine residue at position 205 in the conserved sequence WMAPES is characteristic of pTK's that are receptors.

The Hanks et al article identifies eleven catalytic sub-domains containing pTK consensus residues and sequences. The pTKs of the present invention will have most or all of these consensus residues and sequences.

Some particularly strongly conserved residues and sequences are shown in Table 1.

TABLE 1

| Conserved Residues and Sequences in pTKs[1] | | |
|---|---|---|
| Position[2] | Residue or Sequence | Catalytic Domain |
| 50 | G | I |
| 52 | G | I |
| 57 | V | I |
| 70 | A | II |
| 72 | K | II |
| 91 | E | III |
| 166 | D | VI |
| 171 | N | VI |
| 184–186 | DFG | VII |
| 208 | E | VIII |
| 220 | D | IX |
| 225 | G | IX |
| 280 | R | XI |

1. See Hanks et al., Science 241, 42-52 (1988)
2. Adjusted in accordance with Hanks et al., Id.

A pTK of the invention may contain all thirteen of these highly conserved residues and sequences. As a result of natural or synthetic mutations, the pTKs of the invention may contain fewer than all thirteen strongly conserved residues and sequences, such as 11, 9, or 7 such sequences.

The receptors of the invention generally belong to the same class of pTK sequences that c-kit belongs to. It has surprisingly been discovered, however, that a new functional class of receptor pTKs exists. The new functional class of receptor pTKs is expressed in primitive hematopoietic cells, but not expressed in mature hematopoietic cells.

For the purpose of this specification, a primitive hematopoietic cell is totipotent, i.e. capable of reconstituting all hematopoietic blood cells in vivo. A mature hematopoietic cell is non-self-renewing, and has limited proliferative capacity—i.e., a limited ability to give rise to multiple lineages. Mature hematopoietic cells, for the purposes of this specification, are generally capable of giving rise to only one or two lineages in vitro or in vivo.

It should be understood that the hematopoietic system is complex, and contains many intermediate cells between the primitive totipotent hematopoietic stem cell and the totally committed mature hematopoietic cells defined above. As the stem cell develops into increasingly mature, lineage-restricted cells, it gradually loses its capacity for self-renewal.

The receptors of the present invention may and may not be expressed in these intermediate cells. The necessary and sufficient condition that defines members of the new class of receptors is that they are present in the primitive, totipotent stem cell or cells, and not in mature cells restricted only to one or, at most, two lineages.

An example of a member of the new class of receptor pTKs is called fetal liver kinase 2 (flk-2) after the organ in which it was found. There is approximately 1 totipotent stem cell per $10^4$ cells in mid-gestation (day 14) fetal liver in mice. In addition to fetal liver, flk-2 is also expressed in fetal spleen, fetal thymus, adult brain, and adult marrow.

For example, flk-2 is expressed in individual multipotential CFU-Blast colonies capable of generating numerous multilineage colonies upon replating. It is likely, therefore, that flk-2 is expressed in the entire primitive (i.e. self-renewing) portion of the hematopoietic hierarchy. This discovery is consistent with flk-2 being important in transducing putative self-renewal signals from the environment.

It is particularly relevant that the expression of flk-2 mRNA occurs in the most primitive thymocyte subset. Even in two closely linked immature subsets that differ in expression of the IL-2 receptor, flk-2 expression segregates to the more primitive subset lacking an IL-2 receptor. The earliest thymocyte subset is believed to be uncommitted. Therefore, the thymocytes expressing flk-2 may be multipotential. flk-2 is the first receptor tyrosine kinase known to be expressed in the T-lymphoid lineage.

The fetal liver mRNA migrates relative to 28S and 18S ribosomal bands on formaldehyde agarose gels at approximately 3.5 kb while the brain message is considerably larger. In adult tissues, flk-2 m-RNA from both brain and bone marrow migrated at approximately 3.5 kb.

A second pTK receptor is also included in the present invention. This second receptor, which is called fetal liver kinase 1 (flk-1), is not a member of the same class of receptors as flk-2, since flk-1 may be found in some more mature hematopoietic cells. The amino acid sequence of flk-1 is given in FIG. 2 (SEQ ID NO:4).

The present invention includes the flk-1 receptor as well as DNA, cDNA and RNA encoding flk-1. The DNA sequence of flk-1 is also given in FIG. 2. Flk-1 may be found in the same organs as flk-2, as well as in fetal brain, stomach, kidney, lung, heart and intestine; and in adult kidney, heart, spleen, lung, muscle, and lymph nodes.

The receptor protein tyrosine kinases of the invention are known to be divided into easily found domains. The DNA sequence corresponding to the pTKs encode, starting at their 5'-ends, a hydrophobic leader sequence followed by a hydrophilic extracellular domain, which binds to, and is activated by, a specific ligand. Immediately downstream from the extracellular receptor domain, is a hydrophobic transmembrane region. The transmembrane region is immediately followed by a basic catalytic domain, which may easily be identified by reference to the Hanks et al. and Wilks articles discussed above.

The present invention includes the extracellular receptor domain lacking the transmembrane region and catalytic domain. Preferably, the hydrophobic leader sequence is also removed from the extracellular domain. In the case of flk-2, the hydrophobic leader sequence includes amino acids 127.

These regions and domains may easily be visually identified by those having ordinary skill in the art by reviewing the amino acid sequence in a suspected pTKs and comparing it to known pTKs. For example, referring to FIG. 1, the transmembrane region of flk-2, which separates the extracellular receptor domain from the catalytic domain, is encoded by nucleotides 1663 (T) to 1722 (C). These nucleotides correspond to amino acid residues 545 (Phe) to 564 (Cys). The amino acid sequence between the transmembrane region and the catalytic sub-domain (amino acids 618–623) identified by Hanks et al. as sub-domain I (i.e., GXGXXG) is characteristic of receptor protein tyrosine kinases.

The extracellular domain may also be identified through commonly recognized criteria of extracellular amino acid sequences. The determination of appropriate criteria is known to those skilled in the art, and has been described, for example, by Hopp et al, Proc. Nat'l Acad. Sci. USA 78, 3824–3828 (1981); Kyte et al, J. Mol. Biol. 157, 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed characteristic of extracellular domains.

As will be discussed in more detail below, the nucleic acid molecules that encode the receptors of the invention may be inserted into known vectors for use in standard recombinant DNA techniques. Standard recombinant DNA techniques are those such as are described in Sambrook et al., "Molecular Cloning," Second Edition, Cold Spring Harbor Laboratory Press (1987) and by Ausubel et al., Eds, "Current Protocols in Molecular Biology," Green Publishing Associates and Wiley-Interscience, New York (1987). The vectors may be circular (i.e. plasmids) or non-circular. Standard vectors are available for cloning and expression in a host. The host may be prokaryotic or eucaryotic. Prokaryotic hosts are preferably *E. coli*. Preferred eucaryotic hosts include yeast, insect and mammalian cells. Preferred mammalian cells include, for example, CHO, COS and human cells.

Ligands

The invention also includes ligands that bind to the receptor pTKs of the invention. In addition to binding, the ligands stimulate the proliferation of additional primitive stem cells, differentiation into more mature progenitor cells, or both.

The ligand may be a growth factor that occurs naturally in a mammal, preferably the same mammal that produces the corresponding receptor. The growth factor may be isolated and purified, or be present on the surface of an isolated population of cells, such as stromal ells.

The ligand may also be a molecule that does not occur naturally in a mammal. For example, antibodies, preferably monoclonal, raised against the receptors of the invention or against anti-ligand antibodies mimic the shape of, and act as, ligands if they constitute the negative image of the receptor or anti-ligand antibody binding site. The ligand may also be a non-protein molecule that acts as a ligand when it binds to, or otherwise comes into contact with, the receptor.

In another embodiment, nucleic acid molecules encoding the ligands of the invention are provided. The nucleic acid molecule may be RNA, DNA or cDNA.

Stimulating Proliferation of Stem Cells

The invention also includes a method of stimulating the proliferation and/or differentiation of primitive mammalian hematopoietic stem cells as defined above. The method comprises contacting the stem cells With a ligand in accordance with the present invention. The stimulation of proliferation and/or differentiation may occur in vitro or in vivo.

The ability of a ligand according to the invention to stimulate proliferation of stem cells in vitro and in vivo has important therapeutic applications. Such applications include treating mammals, including humans, whose primitive stem cells do not sufficiently undergo self-renewal. Example of such medical problems include those that occur when defects in hematopoietic stem cells or their related growth factors depress the number of white blood cells. Examples of such medical problems include anemia, such as macrocytic and aplastic anemia. Bone marrow damage resulting from cancer chemotherapy and radiation is another example of a medical problem that would be helped by the stem cell factors of the invention.

Functional Equivalents

The invention includes functional equivalents of the pTK receptors, receptor domains, and ligands described above as well as of the nucleic acid sequences encoding them. A protein is considered a functional equivalent of another protein for a specific function if the equivalett protein is immunologically cross-reactive with, and has the same function as, the receptors and ligands of the invention. The equivalent may, for example, be a fragment of the protein, or a substitution, addition or deletion mutant of the protein.

For example, it is possible to substitute amino acids in a sequence with equivalent amino acids. Groups of amino acids known normally to be equivalent are:
(a) Ala(A) Ser(S) Thr(T) Pro(P) Gly(G);
(b) Asn(N) Asp(D) Glu(E) Gln(Q);
(c) His(H) Arg(R) Lys(K);
(d) Met(M) Leu(L) Ile(I) Val(V); and
(e) Phe(F) Tyr(Y) Trp(W).

Substitutions, additions and/or deletions in the receptors and ligands may be made as long as the resulting equivalent receptors and ligands are immunologically cross reactive with, and have the same function as, the native receptors and ligands.

The equivalent receptors and ligands will normally have substantially the same amino acid sequence as the native receptors and ligands. An amino acid sequence that is substantially the same as another sequence, but that differs from the other sequence by means of one or more substitutions, additions and/or deletions is considered to be an equivalent sequence. Preferably, less than 25%, more preferably less than 10%, and most preferably less than 5% of the number of amino acid residues in the amino acid sequence of the native receptors and ligands are substituted for, added to, or deleted from.

Equivalent nucleic acid molecules include nucleic acid sequences that encode equivalent receptors and ligands as defined above. Equivalent nucleic acid molecules also include nucleic acid sequences that differ from native nucleic acid sequences in ways that do not affect the corresponding amino acid sequences.

ISOLATION OF NUCLEIC ACID MOLECULES AND PROTEINS

Isolation of Nucleic Acid Molecules Encoding Receptors

In order to produce nucleic acid molecules encoding mammalian stem cell receptors, a source of stem cells is provided. Suitable sources include fetal liver, spleen, or thymus cells or adult marrow or brain cells.

For example, suitable mouse fetal liver cells may be obtained at day 14 of gestation. Mouse fetal thymus cells may be obtained at day 14–18, preferably day 15, of gestation. Suitable fetal cells of other mammals are obtained at gestation times corresponding to those of mouse.

Total RNA is prepared by standard procedures from stem cell receptor-containing tissue. The total RNA is used to direct cDNA synthesis. Standard methods for isolating RNA and synthesizing cDNA are provided in standard manuals of molecular biology such as, for example, in Sambrook et al., "Molecular Cloning," Second Edition, Cold Spring Harbor Laboratory Press (1987) and in Ausubel et al., (Eds), "Current Protocols in Molecular Biology," Greene Associates/Wiley Interscience, New York (1990).

The cDNA of the receptors is amplified by known methods. For example, the cDNA may be used as a template for amplification by polymerase chain reaction (PCR); see Saiki et al., Science, 239, 487 (1988) or Mullis et al., U.S. Pat. No. 4,683,195. The sequences of the oligonucleotide primers for the PCR amplification are derived from the sequences of known receptors, such as from the sequences given in FIGS. 1 and 2 for flk-2 and flk-1, respectively, preferably from flk-2. The oligonucleotides are synthesized by methods known in the art. Suitable methods include those described by Caruthers in Science 230, 281–285 (1985).

In order to isolate the entire protein-coding regions for the receptors of the invention, the upstream oligonucleotide is complementary to the sequence at the 5, end, preferably encompassing the ATG start codon and at least 5–10 nucleotides upstream of the start codon. The downstream oligonucleotide is complementary to the sequence at the 3' end, optionally encompassing the stop codon. A mixture of upstream and downstream oligonucleotides are used in the PCR amplification. The conditions are optimized for each particular primer pair according to standard procedures. The PCR product is analyzed by electrophoresis for the correct size cDNA corresponding to the sequence between the primers.

Alternatively, the coding region may be amplified in two or more overlapping fragments. The overlapping fragments are designed to include a restriction site permitting the assembly of the intact cDNA from the fragments.

The amplified DNA encoding the receptors of the invention may be replicated in a wide variety of cloning vectors in a wide variety of host cells. The host cell may be prokaryotic or eukaryotic. The DNA may be obtained from natural sources and, optionally, modified, or may be synthesized in whole or in part.

The vector into which the DNA is spliced may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages.

Isolation of Receptors

DNA encoding the receptors of the invention are inserted into a suitable vector and expressed in a suitable prokaryotic or eucaryotic host. Vectors for expressing proteins in bacteria, especially *E. coli*, are known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); lambda Pr; maltose binding protein (pMAL); and glutathione S-transferase (pGST) - see Gene 67, 31 (1988) and Peptide Research 3, 167 (1990).

Vectors useful in yeast are available. A suitable example is the 2u plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80. 4654–4659 (1983); G. Urlaub and L. A. Chasin, Proc. Natl. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Vectors containing the receptor-encoding DNA and control signals are inserted into a host cell for expression of the receptor. Some useful expression host cells include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DHI, and *E. coli* MRC1, *Pseudomonas, Bacillus,* such as *Bacillus subtilis,* and *Streptomyces.* Suitable eukaryotic cells include yeast and other fungi, insect, animal cells, such as COS cells and CHO cells, human cells and plant cells in tissue culture.

The human homologs of the mouse receptors described above are isolated by a similar strategy. RNA encoding the receptors are obtained from a source of human cells enriched for primitive stem cells. Suitable human cells include fetal spleen, thymus and liver cells, and umbilical cord blood as well as adult brain and bone marrow cells. The human fetal cells are preferably obtained on the day of gestation corresponding to mid-gestation in mice. The amino acid sequences of the human flk receptors as well as of the nucleic acid sequences encoding them are homologous to the amino acid and nucleotide sequences of the mouse receptors.

In the present specification, the sequence of a first protein, such as a receptor or a ligand, or of a nucleic acid molecule that encodes the protein, is considered homologous to a second protein or nucleic acid molecule if the amino acid or nucleotide sequence of the first protein or nucleic acid molecule is at least about 30% homologous, preferably at least about 50% homologous, and more preferably at least about 65% homologous to the respective sequences of the second protein or nucleic acid molecule. In the case of proteins having high homology, the amino acid or nucleotide sequence of the first protein or nucleic acid molecule is at least about 75% homologous, preferably at least about 85% homologous, and more preferably at least about 95% homologous to the amino acid or nucleotide sequence of the second protein or nucleic acid molecule.

Combinations of mouse oligonucleotide pairs are used as PCR primers to amplify the human homologs from the cells to account for sequence divergence. The remainder of the procedure for obtaining the human flk homologs are similar to those described above for obtaining mouse flk receptors. The less than perfect homology between the human flk homologs and the mouse oligonucleotides is taken into account in determining the stringency of the hybridization conditions.

Assay for expression of Receptors on Stem Cells

In order to demonstrate the expression of flk receptors on the surface of primitive hematopoietic stem cells, antibodies that recognize the receptor are raised. The receptor may be the entire protein as it exists in nature, or an antigenic fragment of the whole protein. Preferably, the fragment comprises the predicted extracellular portion of the molecule.

Antigenic fragments may be identified by methods known in the art. Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp et al, Proc. Nat'l Acad. Sci. USA 78, 3824–3828 (1981); Kyte et al, J. Mol. Biol. 157. 105–132 (1982); Emini, J. Virol. 55, 836–839 (1985); Jameson et al, CA BIOS 4, 181–186 (1988); and Karplus et al, Naturwissenschaften 72, 212–213 (1985). Amino acid domains predicted by these criteria to be surface exposed are selected preferentially over domains predicted to be more hydrophobic or hidden.

The proteins and fragments of the receptors to be used as antigens may be prepared by methods known in the art. Such methods include isolating or synthesizing DNA encoding the proteins and fragments, and using the DNA to produce recombinant proteins, as described above.

Fragments of proteins and DNA encoding the fragments may be chemically synthesized by methods known in the art from individual amino acids and nucleotides. Suitable methods for synthesizing protein fragments are described by Stuart and Young in "Solid Phase Peptide Synthesis," Second Edition, Pierce Chemical Company (1984). Suitable methods for synthesizing NA fragments are described by Caruthers in Science 230, 281–285 (1985).

If the receptor fragment defines the epitope, but is too short to be antigenic, it may be conjugated to a carrier molecule in order to produce antibodies. Some suitable carrier molecules include keyhole limpet hemocyanin, Ig sequences, TrpE, and human or bovine serum albumen. Conjugation may be carried out by methods known in the art. One such method is to combine a cysteine residue of the fragment with a cysteine residue on the carrier molecule.

The antibodies are preferably monoclonal. Monoclonal antibodies may be produced by methods known in the art. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

Polyclonal or monoclonal antisera shown to be reactive with receptor-encoded native proteins, such as with flk-1 and flk-2 encoded proteins, expressed on the surface of viable cells are used to isolate antibody-positive cells. One method for isolating such cells is flow cytometry; see, for example, Loken et al., European patent application 317,156. The cells obtained are assayed for stem cells by engraftment into radiation-ablated hosts by methods known in the art; see, for example, Jordan et al., Cell 61, 953–963 (1990).

Criteria for Novel stem Cell Receptor Tyrosine Kinases Expressed in Stem Cells

Additional novel receptor tyrosine kinase cDNAs are obtained by amplifying cDNAs from stem cell populations using oligonucleotides as PCR primers; see above. Examples of suitable oligonucleotides are PTK1 and PTK2, which were described by Wilks et al. in Proc. Natl. Acad. Sci. USA 86, 1603–1607 (1989). Novel cDNA is selected on the basis of differential hybridization screening with probes representing known kinases. The cDNA clones hybridizing only at low stringency are selected and sequenced. The presence of the amino acid triplet DFG confirms that the sequence represents a kinase. The diagnostic methionine residue in the WMAPES motif is indicative of a receptor-like kinase, as described above. Potentially novel sequences obtained are compared to available sequences using databases such as Genbank in order to confirm uniqueness. Gene-specific oligonucleotides are prepared as described above based on the sequence obtained. The oligonucleotides are used to analyze stem cell enriched and depleted populations for expression. Such cell populations in mice are described, for example, by Jordan et al. in Cell 61, 953–956 (1990); Ikuta et al. in Cell 62, 863–864 (1990); Spangrude et al. in Science 241, 58–62 (1988); and Szilvassy et al. in Blood 74, 930–939 (1989). Examples of such human cell populations are described as $CD33^-CD34^+$ by Andrews et al. in the Journal of Experimental Medicine 169, 1721–1731 (1989). Other human stem cell populations are described, for example, in Civin et al., European Patent Application 395,355 and in Loken et al., European Patent Application 317,156.

Isolating Ligands and Nucleic Acid Molecules Encoding Ligands

Cells that may be used for obtaining ligands include stromal cells, for example stromal cells from fetal liver, fetal spleen, fetal thymus and fetal or adult bone marrow. Cell lines expressing ligands are established and screened.

For example, cells such as stromal (non-hematopoietic) cells from fetal liver are immortalized by known methods. Examples of known methods of immortalizing cells include transduction with a temperature sensitive SV40 T-antigen expressed in a retroviral vector. Infection of fetal liver cells with this virus permits the rapid and efficient establishment of multiple independent cell lines. These lines are screened for ligand activity by methods known in the art, such as those outlined below.

Ligands for the receptors of the invention, such as flk-1 and flk-2, may be obtained from the cells in several ways. For example, a bioassay system for ligand activity employs chimeric tagged receptors; see, for example, Flanagan et al., Cell 63, 185–194 (1990). One strategy measures ligand binding directly via a histochemical assay. Fusion proteins comprising the extracellular receptor domains and secretable alkaline phosphatase (SEAP) are constructed and transfected into suitable cells such as NIH/3T3 or COS cells. Flanagan et al. refer to such DNA or amino acid constructs as APtag followed by the name of the receptor—i.e. APtag-c-kit. The fusion proteins bind with high affinity to cells expressing surface-bound ligand. Binding is detectable by the enzymatic activity of the alkaline phosphatase secreted into the medium. The bound cells, which are often stromal cells, are isolated from the APtag-receptor complex.

For example, some stromal cells that bind APtag-flk1 and APtag-flk2 fusion proteins include mouse fetal liver cells (see example 1); human fetal spleen cells (see example 3); and human fetal liver (example 3). Some stromal fetal thymus cells contain flk-1 ligand (example 3).

To clone the cDNA that encodes the ligand, a cDNA library is constructed from the isolated stromal cells in a suitable expression vector, preferably a phage such as CDM8, pSV Sport (BRL Gibco) or piH3, (Seed et al., Proc. Natl. Acad. Sci. USA 84, 3365-3369 (1987)). The library is transfected into suitable host cells, such as COS cells. Cells containing ligands on their surface are detected by known methods, see above.

In one such method, transfected COS cells are distributed into single cell suspensions and incubated with the secreted alkaline phosphatase-flk receptor fusion protein, which is present in the medium from NIH/3T3 or COS cells prepared by the method described by Flanagan et al., see above. Alkaline phosphatase-receptor fusion proteins that are not bound to the cells are removed by centrifugation, and the cells are panned on plates coated with antibodies to alkaline phosphatase. Bound cells are isolated following several washes with a suitable wash reagent, such as 5% fetal bovine serum in PBS, and the DNA is extracted from the cells. Additional details of the panning method described above may be found in an article by Seed et al., Proc. Natl. Acad. Sci. USA 84, 3365-3369 (1987).

In a second strategy, the putative extracellular ligand binding domains of the receptors are fused to the transmembrane and kinase domains of the human c-fms tyrosine kinase and introduced into 3T3 fibroblasts. The human c-fms kinase is necessary and sufficient to transduce proliferative signals in these cells after appropriate activation i.e. with the flk-1 or flk-2 ligand. The 3T3 cells expressing the chimeras are used to screen putative sources of ligand in a cell proliferation assay.

An alternate approach for isolating ligands using the fusion receptor-expressing 3T3 cells and insertional activation is also possible. A retrovirus is introduced into random chromosomal positions in a large population of these cells. In a small fraction, the retrovirus is inserted in the vicinity of the ligand-encoding gene, thereby activating it. These cells proliferate due to autocrine stimulation of the receptor. The ligand gene is "tagged" by the retrovirus, thus facilitating its isolation.

Examples

Example 1. Cells containing mouse flk-1 and flk-2 ligands. Murine stromal cell line 2018.

In order to establish stromal cell lines, fetal liver cells are disaggregated with collagen and grown in a mixture of Dulbecco's Modified Eagle's Medium (DMEM) and 10% heat-inactivated fetal calf serum at 37° C. The cells are immortalized by standard methods. A suitable method involves introducing DNA encoding a growth regulating- or oncogene-encoding sequence into the target host cell. The DNA may be introduced by means of transduction in a recombinant viral particle or transfection in a plasmid. See, for example, Hammerschmidt et al., Nature 340, 393-397 (1989) and Abcouwer et al, Biotechnology 7, 939-946 (1989). Retroviruses are the preferred viral vectors, although SV40 and Epstein-Barr virus can also serve as donors of the growth-enhancing sequences. A suitable retrovirus is the ecotropic retrovirus containing a temperature sensitive SV40 T-antigen (tsA58) and a G418 resistance gene described by McKay in Cell 66, 713-729 (1991). After several days at 37° C., the temperature of the medium is lowered to 32° C. Cells are selected with G418 (0.5 mg/ml). The selected cells are expanded and maintained.

A mouse stromal cell line produced by this procedure is called 2018 and was deposited on Oct. 30, 1991 in the American Type Culture Collection, Rockville, Md., USA (ATCC); accession number CRL 10907.

Example 2. Cells containing human flk-1 and flk-2 ligands.

Human fetal liver (18, 20, and 33 weeks after abortion), spleen (18 weeks after abortion), or thymus (20 weeks after abortion) is removed at the time of abortion and stored on ice in a balanced salt solution. After mincing into 1 mm fragments and forcing through a wire mesh, the tissue is washed one time in Hanks Balanced Salt Solution (HBSS).

The disrupted tissue is centrifuged at 200 xg for 15 minutes at room temperature. The resulting pellet is resuspended in 10-20 ml of a tissue culture grade trypsin-EDTA solution (Flow Laboratories). The resuspended tissue is transferred to a sterile flask and stirred with a stirring bar at room temperature for 10 minutes. One ml of heat-inactivated fetal bovine calf serum (Hyclone) is added to a final concentration of 10% in order to inhibit trypsin activity. Collagenase type IV (Sigma) is added from a stock solution (10 mg/ml in HBSS) to a final concentration of 100 ug/ml in order to disrupt the stromal cells. The tissue is stirred at room temperature for an additional 2.5 hours; collected by centrifugation (400xg, 15 minutes); and resuspended in "stromal medium," which contains Iscove's modification of DMEM supplemented with 10% heat-inactivated fetal calf serum, 5% heat-inactivated human serum (Sigma), 4 mM L-glutamine, 1x sodium pyruvate, (stock of 100x Sigma), 1x non-essential amino acids (stock of 100x, Flow), and a mixture of antibiotics kanomycin, neomycin, penicillin, streptomycin. Prior to resuspending the pellet in the stromal medium, the pellet is washed one time with HBSS. It is convenient to suspend the cells in 60 ml of medium. The number of cultures depends on the amount of tissue.

Example 3. Isolating Stromal cells

Resuspended Cells (example 2) that are incubated at 37° C. with 5% carbon dioxide begin to adhere to the plastic plate within 10-48 hours. Confluent monolayers may be observed within 7-10 days, depending upon the number of cells plated in the initial innoculum. Non-adherent and highly refractile cells adhering to the stromal cell layer as colonies are separately removed by pipetting and frozen. Non-adherent cells are likely sources of populations of self-renewing stem cells containing flk-2. The adherent stromal cell layers are frozen in aliquots for future studies or expanded for growth in culture.

An unexpectedly high level of APtag-flk-2 fusion protein binding to the fetal spleen cells is observed. Two fetal spleen lines are grown in "stromal medium," which is described in example 2.

Non-adherent fetal stem cells attach to the stromal cells and form colonies (colony forming unit - CFU). Stromal cells and CFU are isolated by means of sterile glass cylinders and expanded in culture. A clone, called Fsp 62891, contains the flk-2 ligand. Fsp 62891 was deposited in the American Type Culture Collection, Rockville, Md., U.S.A on Nov. 21, 1991, accession number CRL 10935.

Fetal liver and fetal thymus cells are prepared in a similar way. Both of these cell types produce ligands of flk-1 and, in the case of liver, some flk-2. One such fetal thymus cell line, called F.thy 62891, was deposited in the American Type Culture Collection, Rockville, Md., U.S.A on Nov. 21, 1991, accession number CRL 10936.

Human cell lines are prepared from fetal cells with the same temperature sensitive immortalizing virus used to prepare the murine cell line described in example 1.

Example 4. Isolation of human stromal cell clone

Highly refractile cells overgrow patches of stromal cells, presumably because the stromal cells produce factors that allow the formation of the CFU. To isolate stromal cell clones, sterile glass cylinders coated with vacuum grease are positioned over the CFU. A trypsin-EDTA solution (100 ml) is added in order to detach the cells. The cells are added to 5 ml of stromal medium and each (clone) plated in a single well of 6-well plate.

Example 5. Plasmid (AP-tag) for expressing secretable alkaline phosphatase (SEAP)

Plasmids that express secretable alkaline phosphatase are described by Flanagan and Leder in Cell 63, 185–194 (1990). The plasmids contain a promoter, such as the LTR promoter; a polylinker, including HindIII and BglII; DNA encoding SEAP; a poly-A signal; and ampicillin resistance gene; and replication site.

Example 6. Plasmid for expressing APtag-flk-2 and APtag-flk-1 fusion proteins Plasmids that express fusion proteins of SEAP and the extracellular portion of either flk-1 or flk-2 are prepared in accordance with the protocols of Flanagan and Leder in Cell 63, 185–194 (1990) and Berger et al., Gene 66, 1–10 (1988). Briefly, a HindIIIBam HI fragment containing the extracellular portion of flk-1 or flk-2 is prepared and inserted into the HindIII-BglII site of the plasmid described in example 5.

Example 7. Production Of APtag-flk-1 Or -flk-2 Fusion Protein

The plasmids from Example 6 are transfected into Cos-7 cells by DEAE-dextran (as described in Current Protocols in Molecular Biology, Unit 16.13, "Transient Expression of Proteins Using Cos Cells," 1991); and cotransfected with a selectable marker, such as pSV7neo, into NIH/3T3 cells by calcium precipitation. The NIH/3T3 cells are selected with 600$\mu$g/ml G418 in 100 mm plates. Over 300 clones are screened for secretion of placental alkaline phosphatase activity. The assay is performed by heating a portion of the supernatant at 65° C. for 10 minutes to inactivate background phosphatase activity, and measuring the OD$_{405}$ after incubating with 1M diethanolamine (pH 9.8), 0.5 mM MgCl$_2$, 10 mM L-homoarginine (a phosphatase inhibitor), 0.5 mg/ml BSA, and 12 mM p-nitrophenyl phosphate. Human placental alkaline phosphatase is used to perform a standard curve. The APtag-flk-1 clones (F-1AP21-4) produce up to 10 $\mu$g alkaline phosphatase activity/ml and the APtag-flk-2 clones (F-2AP26-0) produce up to 0.5 $\mu$g alkaline phosphatase activity/ml.

Example 8. Assay For APtag-flk-1 Or APtag-flk-2 Binding To Cells

Figure 4:
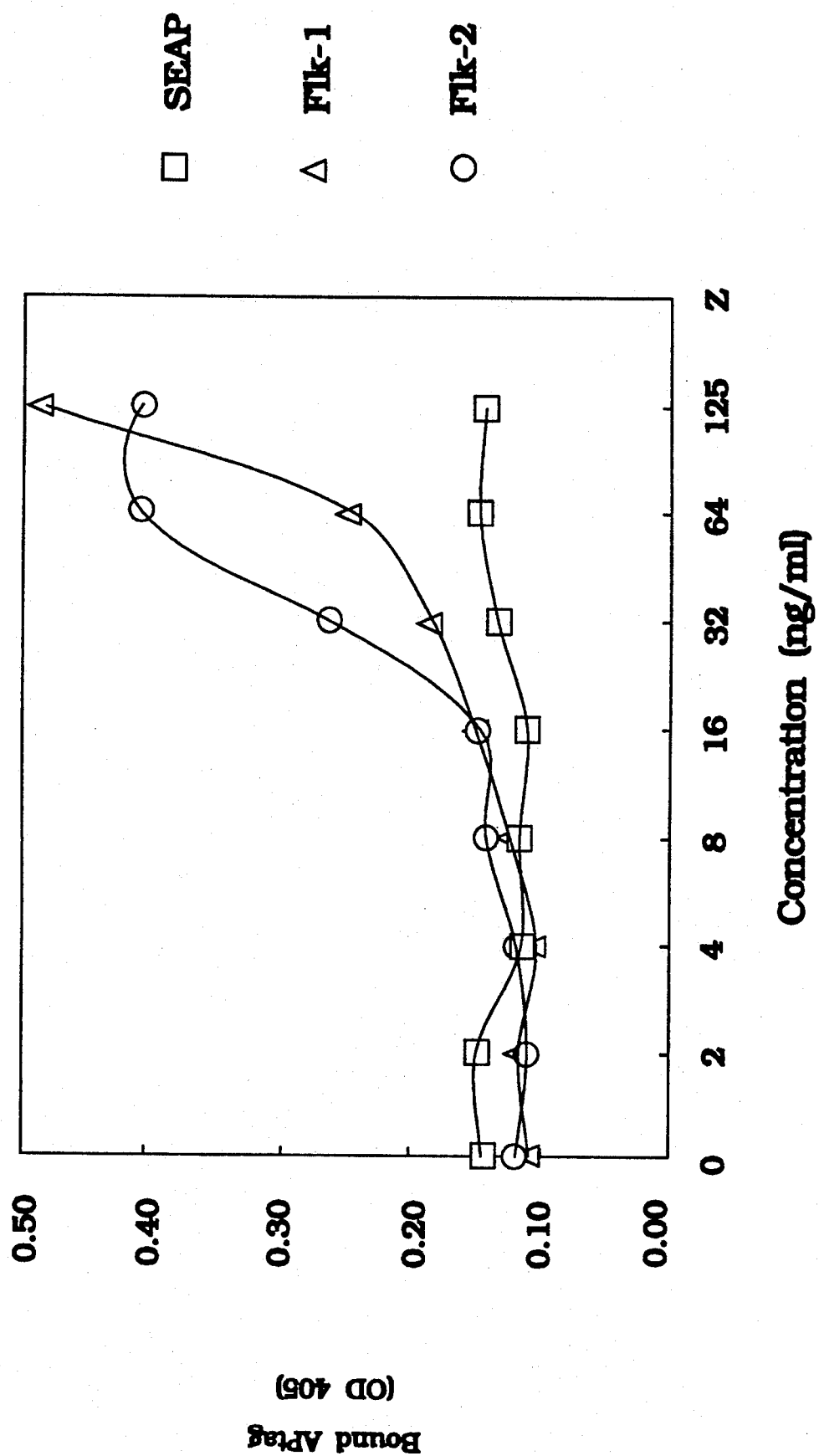
FIG. 4 shows the dose response of binding between stromal cells (2018) and APtag-flk-2 as well as APtag-flk-1. APtag without receptor (SEAP) is used as a control. See Example 8.

The binding of APtag-flk-1 or APtag-flk-2 to cells containing the appropriate ligand is assayed by standard methods. See, for example, Flanagan and Leder, Cell 63:185–194, 1990). Cells (i.e., mouse stromal cells, human fetal liver, spleen or thymus, or various control cells) are grown to confluency in six-well plates and washed with HBHA (Hank's balanced salt solution with 0.5 mg/ml BSA, 0.02% NaN$_3$, 20 mM HEPES, pH 7.0). Supernatants from transfected COS or NIH/3T3 cells containing either APtag-flk-1 fusion protein, APtag-flk-2 fusion protein, or APtag without a receptor (as a control) are added to the cell monolayers and incubated for two hours at room temperature on a rotating platform. The concentration of the APtag-flk-1 fusion protein, APtag-flk-2 fusion protein, or APtag without a receptor is 60 ng/ml of alkaline phosphatase as determined by the standard alkaline phosphatase curve (see above). The cells are then rinsed seven times with HBHA and lysed in 350 $\mu$l of 1% Triton X-100, 10 mM Tris-HCl (pH 8.0). The lysates re transferred to a microfuge tube, along with a further 150 $\mu$l rinse with the same solution. After vortexing vigorously, the samples are centrifuged for five minutes in a microfuge, heated at 65° C. for 12 minutes to inactivate cellular phosphatases, and assayed for phosphatase activity as described previously. Results of experiments designed to show the time and dose responses of binding between stromal cells containing the ligands to flk-2 and flk-1 (2018) and APtag-flk-2, APtag-flk-1 and APtag without receptor (as a control) are shown in FIGS. 3 and 4, respectively.

Example 9. Cloning and Expression of cDNA Coding For Mouse Ligand To flk-1 and flk-2 Receptors cDNA expressing mouse ligand for flk-1 and flk-2 is prepared by known methods. See, for example, Seed, B., and Aruffo, A. PNAS 84:3365–3369, 1987; Simmons, D. and Seed, B. J. Immunol. 141:2797–2800; and D'Andrea, A. D., Lodish, H. F. and Wong, G. G. Cell 57:277–285, 1989).

The protocols are listed below in sequence: (a) RNA isolation; (b) poly A RNA preparation; (c) cDNA synthesis; (d) cDNA size fractionation; (e) propagation of plasmids (vector); (f) isolation of plasmid DNA; (g) preparation of vector pSV Sport (BRL Gibco) for cloning; (h) compilation of buffers for the above steps; (i) Transfection of cDNA encoding Ligands in Cos 7 Cells; (j) panning procedure.

9a. Guanidinium thiocyanate/LiCl Protocol for RNA Isolation

For each ml of mix desired, 0.5 g guanidine thiocyanate (GuSCN) is dissolved in 0.55 ml of 25% LiCl (stock filtered through 0.45 micron filter). 20 $\mu$l of mercaptoethanol is added. (The resulting solution is not good for more than about a week at room temperature.)

The 2018 cells are centrifuged, and 1 ml of the solution described above is added to up to $5 \times 10^7$ cells. The cells are sheared by means of a polytron until the mixture is non-viscous. For small scale preparations (<$10^8$ cells), the sheared mixture is layered on 1.5 ml of 5.7M CsCl (RNase free; 1.26 g CsCl added to every ml 10 mM EDTA pH8), and overlaid with RNase-free water if needed. The mixture is spun in an SW55 rotor at 50 krpm for 2 hours. For large scale preparations, 25 ml of the mixture is layered on 12 ml CsCl in an SW28 tube, overlaid as above, and spun at 24 krpm for 8 hours. The contents of the tube are aspirated carefully with a sterile pasteur pipet connected to a vacuum flask. Once past the CsCl interface, a band around the tube is scratched with the pipet tip to prevent creeping of the layer on the wall down the tube. The remaining CsCl solution is aspirated. The resulting pellet is taken up in water, but not redissolved. 1/10 volume of sodium acetate and three volumes of ethanol are added to the mixture, and spun. The pellet is resuspended in water at 70o, if necessary. The concentration of the RNA is adjusted to 1 mg/ml and frozen.

It should be noted that small RNA molecules (e.g., 5S) do not come down. For small amounts of cells, the volumes are scaled down, and the mixture is overlaid with GuSCN in RNase-free water on a gradient (precipitation is inefficient when RNA is dilute).

9b. Poly A RNA preparation (All buffers mentioned are compiled separately below)

A disposable polypropylene column is prepared by washing with 5M NaOH and then rinsing with RNase-free water. For each milligram of total RNA, approximately 0.3 ml (final packed bed) of oligo dT cellulose is added. The oligo dT cellulose is prepared by resuspending approximately 0.5 ml of dry powder in 1 ml of 0.1M NaOH and transferring it into the column, or by percolating 0.1M NaOH through a previously used column. The column is washed with several column volumes of RNase-free water until the pH is neutral, and rinsed with 2-3 ml of loading buffer. The column bed is transferred to a sterile 15 ml tube using 4-6 ml of loading buffer.

Total RNA from the 2018 cell line is heated to 70° C. for 2-3 minutes. LiCl from RNase-free stock is added to the mixture to a final concentration of 0.5M. The mixture is combined with oligo dT cellulose in the 15 ml tube, which is vortexed or agitated for 10 minutes. The mixture is poured into the column, and washed with 3 ml loading buffer, and then with 3 ml of middle wash buffer. The mRNA is eluted directly into an SW55 tube with 1.5 ml of 2 mM EDTA and 0.1% SDS, discarding the first two or three drops.

The eluted mRNA is precipitated by adding 1/10 volume of 3M sodium acetate and filling the tube with ethanol. The contents of the tube are mixed, chilled for 30 minutes at $-20°$, and spun at 50 krpm at 5° C. for 30 minutes. After the ethanol is decanted, and the tube air dried, the mRNA pellet is resuspended in 50-100 $\mu$l of RNase-free water. 5 of the resuspended mRNA is heated to 70° C. in MOPS/EDTA/formaldehyde, and examined on an RNase-free 1% agarose gel.

9c. cDNA Synthesis

The protocol used is a variation of the method described by Gubler and Hoffman in Gene 25, 263-270 (1983).

1. First Strand. 4 $\mu$g of mRNA is added to a microfuge tube, heated to approximately 100° C. for 30 seconds, quenched on ice. The volume is adjusted to 70$\mu$l with RNAse-free water. 20 $\mu$l of RT1 buffer, 2 $\mu$l of RNAse inhibitor (Boehringer 36 u/$\mu$l ), 1 $\mu$l of 5 $\mu$g/$\mu$l of oligo dT (Collaborative Research), 2.5 $\mu$l of 20 mM dXTP's (ultrapure - US Biochemicals), 1 $\mu$l of 1M DTT and 4 $\mu$l of RT-XL (Life Sciences, 24 u/$\mu$l ) are added. The mixture is incubated at 42° C. for 40 minutes, and inactivated by heating at 70° C. for 10 minutes.

2. Second Strand. 320 $\mu$l of RNAse-free water, 80 $\mu$l of RT2 buffer, 5 $\mu$l of DNA Polymerase I (Boehringer, 5 U/$\mu$l), 2 $\mu$l RNAse H (BRL 2 u/$\mu$l) are added to the solution containing the first strand. The solution is incubated at 15° C. for one hour and at 22° C. for an additional hour. After adding 20 $\mu$l of 0.5M EDTA, pH 8.0, the solution is extracted with phenol and precipitated by adding NaCl to 0.5M linear polyacrylamide (carrier) to 20 $\mu$g/ml, and filling the tube with EtOH. The tube is spun for 2-3 minutes in a microfuge, vortexed to dislodge precipitated material from the wall of the tube, and respun for one minute.

3. Adaptors. Adaptors provide specific restriction sites to facilitate cloning, and are available from BRL Gibco, New England Biolabs, etc. Crude adaptors are resuspended at a concentration of 1 $\mu$g/$\mu$l. MgSO$_4$ is added to a final concentration of 10 mM, followed by five volumes of EtOH. The resulting precipitate is rinsed with 70% EtOH and resuspended in TE at a concentration of 1 $\mu$g/$\mu$l. To kinase, 25 $\mu$l of resuspended adaptors is added to 3 $\mu$l of 10X kinasing buffer and 20 units of kinase. The mixture is incubated at 37° C. overnight. The precipitated cDNA is resuspended in 240 $\mu$l of TE (10/1). After adding 30 $\mu$l of 10X low salt buffer, 30 $\mu$l of 10X ligation buffer with 0.1 mM ATP, 3 $\mu$l (2.4 $\mu$g) of kinased 12-mer adaptor sequence, 2 $\mu$l (1.6 $\mu$g) of kinased 8-mer adaptor sequence, and 1 $\mu$l of T4 DNA ligase (BioLabs, 400 u/$\mu$l, or Boehringer, 1 Weiss unit ml), the mixture is incubated at 15° C. overnight. The cDNA is extracted with phenol and precipitated as above, except that the extra carrier is omitted, and resuspended in 100 $\mu$l of TE.

9d. cDNA Size Fractionation.

A 20% KOAc, 2 mM EDTA, 1 $\mu$g/ml ethidium bromide solution and a 5% KOAc, 2 mM EDTA, 1 $\mu$g/ml ethidium bromide solution are prepared. 2.6 ml of the 20% KOAc solution is added to the back chamber of a small gradient maker. Air bubbles are removed from the tube connecting the two chambers by allowing the 20% solution to flow into the front chamber and forcing the solution to return to the back chamber by tilting the gradient maker. The passage between the chambers is closed, and 2.5 ml of 5% solution is added to the front chamber. Any liquid in the tubing from a previous run is removed by allowing the 5% solution to flow to the end of the tubing, and then to return to its chamber. The apparatus is placed on a stirplate, and, with rapid stirring, the topcock connecting the two chambers and the front stopcock are opened. A polyallomer 5W55 tube is filled from the bottom with the KOAc solution. The gradient is overlaid with 100 $\mu$l of cDNA solution, and spun for three hours at 50 k rpm at 22°. To collect fractions from the gradient, the SW55 tube is pierced close to the bottom of the tube with a butterfly infusion set (with the luer hub clipped off). Three 0.5 ml fractions and then six 0.25 ml fractions are collected in microfuge tubes (approximately 22 and 11 drops, respectively). The fractions are precipitated by adding linear polyacrylamide to 20 $\mu$g/ml and filling the tube to the top with ethanol. The tubes are cooled, spun in a microfuge tube for three minutes, vortexed, and respun for one minute. The resulting pellets are rinsed with 70% ethanol and respun, taking care not to permit the pellets to dry to completion. Each 0.25 ml fraction is resuspended in 10 $\mu$l of TE, and 1 $\mu$l is run on a 1% agarose minigel. The first three fractions, and the last six which contain no material smaller than 1 kb are pooled.

9e. Propagation of Plasmids

SupF plasmids are selected in nonsuppressing bacterial hosts containing a second plasmid, p3, which contains amber mutated ampicillin and tetracycline drug resistance elements. See Seed, Nucleic Acids Res., 11, 2427-2445 (1983). The p3 plasmid is derived from RPI, is 57 kb in length, and is a stably maintained, single copy episome. The ampicillin resistance of this plasmid reverts at a high rate so that amp$^r$ plasmids usually cannot be used in p3-containing strains. Selection for tetracycline resistance alone is almost as good as selection for ampicillin-tetracycline resistance. However, spontaneous appearance of chromosomal suppressor tRNA mutations presents an unavoidable background (frequency about $10^{-9}$) in this system. Colonies arising from spontaneous suppressor mutations are usually larger than colonies arising from plasmid transformation. Suppressor plasmids are selected in Luria broth (LB) medium containing ampicillin at 12.5 µg/ml and tetr2acycline at 7.5 µg/ml. For scaled-up plasmid preparations, M9 Casamino acids medium containing glycerol (0.8%) is employed as a carbon source. The bacteria are grown to saturation.

Alternatively, pSV Sport (BRL, Gaithersberg, Md.) may be employed to provide SV40 derived sequences for replication, transcription initiation and termination in COS 7 cells, as well as those sequences necessary for replication and ampicillin resistance in *E. coli*.

9f. Isolation of Vector DNA/Plasmid

One liter of saturated bacterial cells are spun down in J6 bottles at 4.2k rpm for 25 minutes. The cells are resuspended in 40 ml 10 mM EDTA, pH 8. 80 ml 0.2M NaOH and 1% SDS are added, and the mixture is swirled until it is clear and viscous. 40 ml 5M KOAc, pH 4.7 (2.5M KOAc, 2.5M HOAc) is added, and the mixture is shaken semi-vigorously until the lumps are approximately 2-3 mm in size. The bottle is spun at 4.2 k rpm for 5 minutes. The supernatant is poured through cheesecloth into a 250 ml bottle, which is then filled with isopropyl alcohol and centrifuged at 4.2 k rpm for 5 minutes. The bottle is gently drained and rinsed with 70% ethanol, taking care not to fragment the pellet. After inverting the bottle and removing traces of ethanol, the mixture is resuspended in 3.5 ml Tris base/EDTA (20 mM/10 mM). 3.75 ml of resuspended pellet and 0.75 ml 10 mg/ml ethidium bromide are added to 4.5 g CsCl. VTi80 tubes are filled with solution, and centrifuged for at least 2.5 hours at 80k rpm. Bands are extracted by visible light with 1 ml syringe and 20 gauge or lower needle. The top of the tube is cut off with scissors, and the needle is inserted upwards into the tube at an angle of about 30 degrees with respect to the tube at a position about 3 mm beneath the band, with the bevel of the needle up. After the band is removed, the contents of the tube are poured into bleach. The extracted band is deposited in a 13 ml Sarstedt tube, which is then filled to the top with n-butanol saturated with 1M NaCl extract. If the amount of DNA is large, the extraction procedure may be repeated. After aspirating the butanol into a trap containing 5M NaOH to destroy ethidium, an approximately equal volume of 1M ammonium acetate and approximately two volumes of 95% ethanol are added to the DNA, which is then spun at 10 k rpm for 5 minutes. The pellet is rinsed carefully with 70% ethanol, and dried with a swab or lyophilizer.

9g. Preparation of Vector for Cloning 20 g of vector is cut in a 200 µl reaction with 100 units of BstXI (New York Biolabs) at 50° C. overnight in a well thermostated, circulating water bath. Potassium acetate solutions (5 and 20%) are prepared in 5 W55 tubes as described above. 100 µl of the digested vector is added to each tube and spun for three hours, 50 k rpm at 22° C. Under 300 nm UV light, the desired band is observed to migrate ⅔ of the length of the tube. Forward trailing of the band indicates that the gradient is overloaded. The band is removed with a 1 ml syringe fitted with a 20 gauge needle. After adding linear polyacrylamide and precipitating the plasmid by adding three volumes of ethanol, the plasmid is resuspended in 50 µl of TE. Trial ligations are carried out with a constant amount of vector and increasing amounts of cDNA. Large scale ligation are carried out on the basis of these trial ligations. Usually the entire cDNA prep requires 1-2 µg of cut vector.

| 9h. Buffers | |
|---|---|
| Loading Buffer: | .5M LiCl, 10 mM Tris pH 7.5, 1 mM EDTA .1% SDS. |
| Middle Wash Buffer: | .15M LiCl, 10 mM Tris pH 7.5, 1 mM EDTA .1% SDS. |
| RT1 Buffer: | .25M Tris pH 8.8 (8.2 at 42$^-$, .25M KCl, 30 mM MgCl$_2$. |
| RT2 Buffer: | .1M Tris pH 7.5, 25 mM MgCl2, .5M KCl, .25 mg/ml BSA, 50 mM dithiothreitol (DTT). |
| 10X Low Salt: | 60 mM Tris pH 7.5, 60 mM MgCl$_2$, 50 mM NaCl, 2.5 mg/ml BSA 70 mM DME |
| 10X Ligation Additions: | 1 mM ATP, 20 mM DTT, 1 mg/ml BSA 10 mM spermidine. |
| 10X Kinasing Buffer: | .5M Tris pH 7.5, 10 mM ATP, 20 mM DTT, 10 mM spermidine, 1 mg/ml BSA 100 mM MgCl$_2$ |

9i. Transfection of cDNA encoding Ligands in Cos 7 Cells

Cos 7 cells are split 1:5 into 100 mm plates in Dulbecco's modified Eagles medium (DME)/10% fetal calf serum (FCS), and allowed to grow overnight. 3 ml Tris/DME (0.039M Tris, pH 7.4 in DME) containing 400 µg/ml DEAE-dextran (Sigman, D-9885) is prepared for each 100 mm plate of Cos 7 cells to be transfected. 10 ug of plasmid DNA preparation per plate is added. The medium is removed from the Cos-7 cells and the DNA/DEAE-dextran mixture is added. The cells are incubated for 4.5 hours. The medium is removed from the cells, and replaced with 3 ml of DME containing 2% fetal calf serum (FCS) and 0.1 mM chloroquine. The cells are incubated for one hour. After removing the chloroquine and replacing with 1.5 ml 20% glycerol in PBS, the cells are allowed to stand at room temperature for one minute. 3 ml Tris/DME is added, and the mixture is aspirated and washed two times with Tris/DME. 10 ml DME/10% FCS is added and the mixture is incubated overnight. The transfected Cos 7 cells are split 1:2 into fresh 100 mm plates with (DME)/10% FCS and allowed to grow.

9j. Panning Procedure for Cos 7 cells Expressing Ligand

1) Antibody-coated plates:

Bacteriological 100 mm plates are coated for 1.5 hours with rabbit anti-human placental alkaline phosphatase (Dako, Calif.) diluted 1:500 in 10 ml of 50 mM Tris.HCl, pH 9.5. The plates are washed three times with 0.15M NaCl, and incubated with 3 mg BSA/ml PBS overnight. The blocking solution is aspirated, and the plates are utilized immediately or frozen for later use.

2) Panning cells:

The medium from transfected Cos 7 cells is aspirated, and 3 ml PBS/0.5 mM EDTA/0.02% sodium azide is added. The plates are incubated at 37° C. for thirty minutes in order to detach the cells. The cells are triturated vigorously with a pasteur pipet and collected in a 15 ml centrifuge tube. The plate is washed with a further 2 ml PBS/EDTA/azide solution, which is then added to the centrifuge tube. After centrifuging at 200 xg for five minutes, the cells are resuspended in 3 ml of APtaq-flk-1 (F-1AP21-4) or flk-2 (F-2AP26-0) supernatant from transfected NIH/3T3 cells (see Example 7.), and incubated for 1.5 hours on ice. The cells are centrifuged again at 200 xg for five minutes. The supernatant is aspirated, and the cells are resuspended in 3 ml PBS/EDTA/azide solution. The cell suspension is layered carefully on 3 ml PBS/EDTA/azide/2% Ficoll, and centrifuged at 200 xg for four minutes. The supernatant is aspirated, and the cells are resuspended in 0.5 ml PBS/EDTA/azide solution. The cells are added to the antibody-coated plates containing 4 ml PBS/EDTA/azide/5% FBS, and allowed to stand at room temperature one to three hours. Non-adhering cells are removed by washing gently two or three times with 3 ml PBS/5% FBS.

3) Hirt Supernatant:

0.4 ml 0.6% SDS and 10 mM EDTA are added to the panned plates, which are allowed to stand 20 minutes. The viscous mixture is added by means of a pipet into a microfuge tube. 0.1ml 5M NaCl is added to the tube, mixed, and chilled on ice for at least five hours. The tube is spun for four minutes, and the supernatant is removed carefully. The contents of the tube are extracted with phenol once, or, if the first interface is not clean, twice. Ten micrograms of linear polyacrylamide (or other carrier) is added, and the tube is filled to the top with ethanol. The resulting precipitate is resuspended in 0.1 ml water or TE. After adding 3 volumes of EtOH/NaOAc, the cells are reprecipitated and resuspended in 0.1 ml water or TE. The cDNA obtained is transfected into any suitable *E. coli* host by electroporation. Suitable hosts are described in various catalogs, and include MC1061/p3 or Electromax DH10B Cells of BRL Gibco. The cDNA is extracted by conventional methods.

The above panning procedure is repeated until a pure *E. coli* clone bearing the cDNA as a unique plasmid recombinant capable of transfecting mammalian cells and yielding a positive panning assay is isolated. Normally, three repetitions are sufficient.

Example 10. Expression of Ligand cDNA

The cDNA is sequenced, and expressed in a suitable host cell, such as a mammalian cell, preferably COS, CHO or NIH/3T3 cells. The presence of the ligand is confirmed by demonstrating binding of the ligand to APtag-flk2 fusion protein (see above).

SUPPLEMENTAL ENABLEMENT

The invention as claimed is enabled in accordance with the above specification and readily available references and starting materials. Nevertheless, on Oct. 30, 1991, Applicants deposited with the American Type Culture Collection, Rockville, Md., USA (ATCC) the cell lines listed below:

2018, ATCC accession no. CRL 10907.
Fsp 62891, ATCC accession no. CRL 10935
F.thy 62891, ATCC accession no. CRL 10936

These deposits were made under the provisions of the Budapest Treaty on the International Recognition of the Deposit of Microorganisms for the Purposes of Patent Procedure and the regulations thereunder (Budapest Treaty). This assures maintenance of a visible culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What I claim is:

1. A recombinant nucleic acid molecule that is flk-1 having the sequence shown in FIG. 2 (SEQIDNO:3).

2. An isolated mRNA that encodes the flk-1 protein, said protein having the amino acid sequence shown in FIG. 2 (SEQIDNO:3).

3. A recombinant nucleic acid molecule comprising the sequence shown in FIG. 2 (SEQIDNO:3) from nucleotide 1 to nucleotide 2493.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3453 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..3009

( i x ) FEATURE:
        ( A ) NAME/KEY: matpeptide
        ( B ) LOCATION: 31..3006

( x i ) SEQUENCE DESCRIPTION: SEQ ID NO:1:

```
GCGGCCTGGC TACCGCGCGC TCCGGAGGCC ATG CGG GCG TTG GCG CAG CGC AGC        54
                                    Met Arg Ala Leu Ala Gln Arg Ser
                                     1               5
```

```
GAC CGG CGG CTG CTG CTG CTT GTT GTT TTG TCA GTA ATG ATT CTT GAG         102
Asp Arg Arg Leu Leu Leu Leu Val Val Leu Ser Val Met Ile Leu Glu
     10              15                  20

ACC GTT ACA AAC CAA GAC CTG CCT GTG ATC AAG TGT GTT TTA ATC AGT         150
Thr Val Thr Asn Gln Asp Leu Pro Val Ile Lys Cys Val Leu Ile Ser
 25              30                  35                      40

CAT GAG AAC AAT GGC TCA TCA GCG GGA AAG CCA TCA TCG TAC CGA ATG         198
His Glu Asn Asn Gly Ser Ser Ala Gly Lys Pro Ser Ser Tyr Arg Met
                 45                  50                  55

GTG CGA GGA TCC CCA GAA GAC CTC CAG TGT ACC CCG AGG CGC CAG AGT         246
Val Arg Gly Ser Pro Glu Asp Leu Gln Cys Thr Pro Arg Arg Gln Ser
             60                  65                  70

GAA GGG ACG GTA TAT GAA GCG GCC ACC GTG GAG GTG GCC GAG TCT GGG         294
Glu Gly Thr Val Tyr Glu Ala Ala Thr Val Glu Val Ala Glu Ser Gly
         75              80                  85

TCC ATC ACC CTG CAA GTG CAG CTC GCC ACC CCA GGG GAC CTT TCC TGC         342
Ser Ile Thr Leu Gln Val Gln Leu Ala Thr Pro Gly Asp Leu Ser Cys
         90                  95                 100

CTC TGG GTC TTT AAG CAC AGC TCC CTG GGC TGC CAG CCG CAC TTT GAT         390
Leu Trp Val Phe Lys His Ser Ser Leu Gly Cys Gln Pro His Phe Asp
105                 110                 115                 120

TTA CAA AAC AGA GGA ATC GTT TCC ATG GCC ATC TTG AAC GTG ACA GAG         438
Leu Gln Asn Arg Gly Ile Val Ser Met Ala Ile Leu Asn Val Thr Glu
                 125                 130                 135

ACC CAG GCA GGA GAA TAC CTA CTC CAT ATT CAG AGC GAA CGC GCC AAC         486
Thr Gln Ala Gly Glu Tyr Leu Leu His Ile Gln Ser Glu Arg Ala Asn
             140                 145                 150

TAC ACA GTA CTG TTC ACA GTG AAT GTA AGA GAT ACA CAG CTG TAT GTG         534
Tyr Thr Val Leu Phe Thr Val Asn Val Arg Asp Thr Gln Leu Tyr Val
             155                 160                 165

CTA AGG AGA CCT TAC TTT AGG AAG ATG GAA AAC CAG GAT GCA CTG CTC         582
Leu Arg Arg Pro Tyr Phe Arg Lys Met Glu Asn Gln Asp Ala Leu Leu
     170                 175                 180

TGC ATC TCC GAG GGT GTT CCG GAG CCC ACT GTG GAG TGG GTG CTC TGC         630
Cys Ile Ser Glu Gly Val Pro Glu Pro Thr Val Glu Trp Val Leu Cys
185                 190                 195                 200

AGC TCC CAC AGG GAA AGC TGT AAA GAA GAA GGC CCT GCT GTT GTC AGA         678
Ser Ser His Arg Glu Ser Cys Lys Glu Glu Gly Pro Ala Val Val Arg
                 205                 210                 215

AAG GAG GAA AAG GTA CTT CAT GAG TTG TTC GGA ACA GAC ATC AGA TGC         726
Lys Glu Glu Lys Val Leu His Glu Leu Phe Gly Thr Asp Ile Arg Cys
             220                 225                 230

TGT GCT AGA AAT GCA CTG GGC CGC GAA TGC ACC AAG CTG TTC ACC ATA         774
Cys Ala Arg Asn Ala Leu Gly Arg Glu Cys Thr Lys Leu Phe Thr Ile
             235                 240                 245

GAT CTA AAC CAG GCT CCT CAG AGC ACA CTG CCC CAG TTA TTC CTG AAA         822
Asp Leu Asn Gln Ala Pro Gln Ser Thr Leu Pro Gln Leu Phe Leu Lys
     250                 255                 260

GTG GGG GAA CCC TTG TGG ATC AGG TGT AAG GCC ATC CAT GTG AAC CAT         870
Val Gly Glu Pro Leu Trp Ile Arg Cys Lys Ala Ile His Val Asn His
265                 270                 275                 280

GGA TTC GGG CTC ACC TGG GAG CTG GAA GAC AAA GCC CTG GAG GAG GGC         918
Gly Phe Gly Leu Thr Trp Glu Leu Glu Asp Lys Ala Leu Glu Glu Gly
                 285                 290                 295

AGC TAC TTT GAG ATG AGT ACC TAC TCC ACA AAC AGG ACC ATG ATT CGG         966
Ser Tyr Phe Glu Met Ser Thr Tyr Ser Thr Asn Arg Thr Met Ile Arg
             300                 305                 310

ATT CTC TTG GCC TTT GTG TCT TCC GTG GGA AGG AAC GAC ACC GGA TAT        1014
Ile Leu Leu Ala Phe Val Ser Ser Val Gly Arg Asn Asp Thr Gly Tyr
     315                 320                 325

TAC ACC TGC TCT TCC TCA AAG CAC CCC AGC CAG TCA GCG TTG GTG ACC        1062
Tyr Thr Cys Ser Ser Ser Lys His Pro Ser Gln Ser Ala Leu Val Thr
```

-continued

|     |     |     |     |     | 330 |     |     |     |     | 335 |     |     |     |     | 340 |     |     |      |
|-----|-----|-----|-----|-----|-----|-----|-----|-----|-----|-----|-----|-----|-----|-----|-----|-----|-----|------|
| ATC | CTA | GAA | AAA | GGG | TTT | ATA | AAC | GCT | ACC | AGC | TCG | CAA | GAA | GAG | TAT |     |     | 1110 |
| Ile | Leu | Glu | Lys | Gly | Phe | Ile | Asn | Ala | Thr | Ser | Ser | Gln | Glu | Glu | Tyr |     |     |      |
| 345 |     |     |     |     | 350 |     |     |     |     | 355 |     |     |     |     | 360 |     |     |      |

| GAA | ATT | GAC | CCG | TAC | GAA | AAG | TTC | TGC | TTC | TCA | GTC | AGG | TTT | AAA | GCG | 1158 |
|-----|-----|-----|-----|-----|-----|-----|-----|-----|-----|-----|-----|-----|-----|-----|-----|------|
| Glu | Ile | Asp | Pro | Tyr | Glu | Lys | Phe | Cys | Phe | Ser | Val | Arg | Phe | Lys | Ala |      |
|     |     |     |     | 365 |     |     |     |     | 370 |     |     |     |     | 375 |     |      |

| TAC | CCA | CGA | ATC | CGA | TGC | ACG | TGG | ATC | TTC | TCT | CAA | GCC | TCA | TTT | CCT | 1206 |
|-----|-----|-----|-----|-----|-----|-----|-----|-----|-----|-----|-----|-----|-----|-----|-----|------|
| Tyr | Pro | Arg | Ile | Arg | Cys | Thr | Trp | Ile | Phe | Ser | Gln | Ala | Ser | Phe | Pro |      |
|     |     |     | 380 |     |     |     |     | 385 |     |     |     |     | 390 |     |     |      |

| TGT | GAA | CAG | AGA | GGC | CTG | GAG | GAT | GGG | TAC | AGC | ATA | TCT | AAA | TTT | TGC | 1254 |
|-----|-----|-----|-----|-----|-----|-----|-----|-----|-----|-----|-----|-----|-----|-----|-----|------|
| Cys | Glu | Gln | Arg | Gly | Leu | Glu | Asp | Gly | Tyr | Ser | Ile | Ser | Lys | Phe | Cys |      |
|     |     | 395 |     |     |     |     | 400 |     |     |     |     | 405 |     |     |     |      |

| GAT | CAT | AAG | AAC | AAG | CCA | GGA | GAG | TAC | ATA | TTC | TAT | GCA | GAA | AAT | GAT | 1302 |
|-----|-----|-----|-----|-----|-----|-----|-----|-----|-----|-----|-----|-----|-----|-----|-----|------|
| Asp | His | Lys | Asn | Lys | Pro | Gly | Glu | Tyr | Ile | Phe | Tyr | Ala | Glu | Asn | Asp |      |
|     | 410 |     |     |     |     | 415 |     |     |     |     | 420 |     |     |     |     |      |

| GAC | GCC | CAG | TTC | ACC | AAA | ATG | TTC | ACG | CTG | AAT | ATA | AGA | AAG | AAA | CCT | 1350 |
|-----|-----|-----|-----|-----|-----|-----|-----|-----|-----|-----|-----|-----|-----|-----|-----|------|
| Asp | Ala | Gln | Phe | Thr | Lys | Met | Phe | Thr | Leu | Asn | Ile | Arg | Lys | Lys | Pro |      |
| 425 |     |     |     |     | 430 |     |     |     |     | 435 |     |     |     |     | 440 |      |

| CAA | GTG | CTA | GCA | AAT | GCC | TCA | GCC | AGC | CAG | GCG | TCC | TGT | TCC | TCT | GAT | 1398 |
|-----|-----|-----|-----|-----|-----|-----|-----|-----|-----|-----|-----|-----|-----|-----|-----|------|
| Gln | Val | Leu | Ala | Asn | Ala | Ser | Ala | Ser | Gln | Ala | Ser | Cys | Ser | Ser | Asp |      |
|     |     |     |     | 445 |     |     |     |     | 450 |     |     |     |     | 455 |     |      |

| GGC | TAC | CCG | CTA | CCC | TCT | TGG | ACC | TGG | AAG | AAG | TGT | TCG | GAC | AAA | TCT | 1446 |
|-----|-----|-----|-----|-----|-----|-----|-----|-----|-----|-----|-----|-----|-----|-----|-----|------|
| Gly | Tyr | Pro | Leu | Pro | Ser | Trp | Thr | Trp | Lys | Lys | Cys | Ser | Asp | Lys | Ser |      |
|     |     |     | 460 |     |     |     |     | 465 |     |     |     |     | 470 |     |     |      |

| CCC | AAT | TGC | ACG | GAG | GAA | ATC | CCA | GAA | GGA | GTT | TGG | AAT | AAA | AAG | GCT | 1494 |
|-----|-----|-----|-----|-----|-----|-----|-----|-----|-----|-----|-----|-----|-----|-----|-----|------|
| Pro | Asn | Cys | Thr | Glu | Glu | Ile | Pro | Glu | Gly | Val | Trp | Asn | Lys | Lys | Ala |      |
|     |     | 475 |     |     |     |     | 480 |     |     |     |     | 485 |     |     |     |      |

| AAC | AGA | AAA | GTG | TTT | GGC | CAG | TGG | GTG | TCG | AGC | AGT | ACT | CTA | AAT | ATG | 1542 |
|-----|-----|-----|-----|-----|-----|-----|-----|-----|-----|-----|-----|-----|-----|-----|-----|------|
| Asn | Arg | Lys | Val | Phe | Gly | Gln | Trp | Val | Ser | Ser | Ser | Thr | Leu | Asn | Met |      |
|     | 490 |     |     |     |     | 495 |     |     |     |     | 500 |     |     |     |     |      |

| AGT | GAG | GCC | GGG | AAA | GGG | CTT | CTG | GTC | AAA | TGC | TGT | GCG | TAC | AAT | TCT | 1590 |
|-----|-----|-----|-----|-----|-----|-----|-----|-----|-----|-----|-----|-----|-----|-----|-----|------|
| Ser | Glu | Ala | Gly | Lys | Gly | Leu | Leu | Val | Lys | Cys | Cys | Ala | Tyr | Asn | Ser |      |
| 505 |     |     |     |     | 510 |     |     |     |     | 515 |     |     |     |     | 520 |      |

| ATG | GGC | ACG | TCT | TGC | GAA | ACC | ATC | TTT | TTA | AAC | TCA | CCA | GGC | CCC | TTC | 1638 |
|-----|-----|-----|-----|-----|-----|-----|-----|-----|-----|-----|-----|-----|-----|-----|-----|------|
| Met | Gly | Thr | Ser | Cys | Glu | Thr | Ile | Phe | Leu | Asn | Ser | Pro | Gly | Pro | Phe |      |
|     |     |     |     | 525 |     |     |     |     | 530 |     |     |     |     | 535 |     |      |

| CCT | TTC | ATC | CAA | GAC | AAC | ATC | TCC | TTC | TAT | GCG | ACC | ATT | GGG | CTC | TGT | 1686 |
|-----|-----|-----|-----|-----|-----|-----|-----|-----|-----|-----|-----|-----|-----|-----|-----|------|
| Pro | Phe | Ile | Gln | Asp | Asn | Ile | Ser | Phe | Tyr | Ala | Thr | Ile | Gly | Leu | Cys |      |
|     |     |     | 540 |     |     |     |     | 545 |     |     |     |     | 550 |     |     |      |

| CTC | CCC | TTC | ATT | GTT | GTT | CTC | ATT | GTG | TTG | ATC | TGC | CAC | AAA | TAC | AAA | 1734 |
|-----|-----|-----|-----|-----|-----|-----|-----|-----|-----|-----|-----|-----|-----|-----|-----|------|
| Leu | Pro | Phe | Ile | Val | Val | Leu | Ile | Val | Leu | Ile | Cys | His | Lys | Tyr | Lys |      |
|     |     | 555 |     |     |     |     | 560 |     |     |     |     | 565 |     |     |     |      |

| AAG | CAA | TTT | AGG | TAC | GAG | AGT | CAG | CTG | CAG | ATG | ATC | CAG | GTG | ACT | GGC | 1782 |
|-----|-----|-----|-----|-----|-----|-----|-----|-----|-----|-----|-----|-----|-----|-----|-----|------|
| Lys | Gln | Phe | Arg | Tyr | Glu | Ser | Gln | Leu | Gln | Met | Ile | Gln | Val | Thr | Gly |      |
|     | 570 |     |     |     |     | 575 |     |     |     |     | 580 |     |     |     |     |      |

| CCC | CTG | GAT | AAC | GAG | TAC | TTC | TAC | GTT | GAC | TTC | AGG | GAC | TAT | GAA | TAT | 1830 |
|-----|-----|-----|-----|-----|-----|-----|-----|-----|-----|-----|-----|-----|-----|-----|-----|------|
| Pro | Leu | Asp | Asn | Glu | Tyr | Phe | Tyr | Val | Asp | Phe | Arg | Asp | Tyr | Glu | Tyr |      |
| 585 |     |     |     |     | 590 |     |     |     |     | 595 |     |     |     |     | 600 |      |

| GAC | CTT | AAG | TGG | GAG | TTC | CCG | AGA | GAG | AAC | TTA | GAG | TTT | GGG | AAG | GTC | 1878 |
|-----|-----|-----|-----|-----|-----|-----|-----|-----|-----|-----|-----|-----|-----|-----|-----|------|
| Asp | Leu | Lys | Trp | Glu | Phe | Pro | Arg | Glu | Asn | Leu | Glu | Phe | Gly | Lys | Val |      |
|     |     |     |     | 605 |     |     |     |     | 610 |     |     |     |     | 615 |     |      |

| CTG | GGG | TCT | GGC | GCT | TTC | GGG | AGG | GTG | ATG | AAC | GCC | ACG | GCC | TAT | GGC | 1926 |
|-----|-----|-----|-----|-----|-----|-----|-----|-----|-----|-----|-----|-----|-----|-----|-----|------|
| Leu | Gly | Ser | Gly | Ala | Phe | Gly | Arg | Val | Met | Asn | Ala | Thr | Ala | Tyr | Gly |      |
|     |     |     | 620 |     |     |     |     | 625 |     |     |     |     | 630 |     |     |      |

| ATT | AGT | AAA | ACG | GGA | GTC | TCA | ATT | CAG | GTG | GCG | GTG | AAG | ATG | CTA | AAA | 1974 |
|-----|-----|-----|-----|-----|-----|-----|-----|-----|-----|-----|-----|-----|-----|-----|-----|------|
| Ile | Ser | Lys | Thr | Gly | Val | Ser | Ile | Gln | Val | Ala | Val | Lys | Met | Leu | Lys |      |
|     |     | 635 |     |     |     |     | 640 |     |     |     |     | 645 |     |     |     |      |

| GAG | AAA | GCT | GAC | AGC | TGT | GAA | AAA | GAA | GCT | CTC | ATG | TCG | GAG | CTC | AAA | 2022 |
|-----|-----|-----|-----|-----|-----|-----|-----|-----|-----|-----|-----|-----|-----|-----|-----|------|
| Glu | Lys | Ala | Asp | Ser | Cys | Glu | Lys | Glu | Ala | Leu | Met | Ser | Glu | Leu | Lys |      |
|     |     |     | 650 |     |     |     |     | 655 |     |     |     |     | 660 |     |     |      |

| | |
|---|---|
| ATG ATG ACC CAC CTG GGA CAC CAT GAC AAC ATC GTG AAT CTG CTG GGG<br>Met Met Thr His Leu Gly His His Asp Asn Ile Val Asn Leu Leu Gly<br>665                              670                        675                        680 | 2070 |
| GCA TGC ACA CTG TCA GGG CCA GTG TAC TTG ATT TTT GAA TAT TGT TGC<br>Ala Cys Thr Leu Ser Gly Pro Val Tyr Leu Ile Phe Glu Tyr Cys Cys<br>                        685                        690                        695 | 2118 |
| TAT GGT GAC CTC CTC AAC TAC CTA AGA AGT AAA AGA GAG AAG TTT CAC<br>Tyr Gly Asp Leu Leu Asn Tyr Leu Arg Ser Lys Arg Glu Lys Phe His<br>                700                        705                        710 | 2166 |
| AGG ACA TGG ACA GAG ATT TTT AAG GAA CAT AAT TTC AGT TCT TAC CCT<br>Arg Thr Trp Thr Glu Ile Phe Lys Glu His Asn Phe Ser Ser Tyr Pro<br>            715                        720                        725 | 2214 |
| ACT TTC CAG GCA CAT TCA AAT TCC AGC ATG CCT GGT TCA CGA GAA GTT<br>Thr Phe Gln Ala His Ser Asn Ser Ser Met Pro Gly Ser Arg Glu Val<br>      730                        735                        740 | 2262 |
| CAG TTA CAC CCG CCC TTG GAT CAG CTC TCA GGG TTC AAT GGG AAT TCA<br>Gln Leu His Pro Pro Leu Asp Gln Leu Ser Gly Phe Asn Gly Asn Ser<br>745                              750                        755                        760 | 2310 |
| ATT CAT TCT GAA GAT GAG ATT GAA TAT GAA AAC CAG AAG AGG CTG GCA<br>Ile His Ser Glu Asp Glu Ile Glu Tyr Glu Asn Gln Lys Arg Leu Ala<br>                        765                        770                        775 | 2358 |
| GAA GAA GAG GAG GAA GAT TTG AAC GTG CTG ACG TTT GAA GAC CTC CTT<br>Glu Glu Glu Glu Glu Asp Leu Asn Val Leu Thr Phe Glu Asp Leu Leu<br>            780                        785                        790 | 2406 |
| TGC TTT GCG TAC CAA GTG GCC AAA GGC ATG GAA TTC CTG GAG TTC AAG<br>Cys Phe Ala Tyr Gln Val Ala Lys Gly Met Glu Phe Leu Glu Phe Lys<br>            795                        800                        805 | 2454 |
| TCG TGT GTC CAC AGA GAC CTG GCA GCC AGG AAT GTG TTG GTC ACC CAC<br>Ser Cys Val His Arg Asp Leu Ala Ala Arg Asn Val Leu Val Thr His<br>      810                        815                        820 | 2502 |
| GGG AAG GTG GTG AAG ATC TGT GAC TTT GGA CTG GCC CGA GAC ATC CTG<br>Gly Lys Val Val Lys Ile Cys Asp Phe Gly Leu Ala Arg Asp Ile Leu<br>825                              830                        835                        840 | 2550 |
| AGC GAC TCC AGC TAC GTC GTC AGG GGC AAC GCA CGG CTG CCG GTG AAG<br>Ser Asp Ser Ser Tyr Val Val Arg Gly Asn Ala Arg Leu Pro Val Lys<br>                        845                        850                        855 | 2598 |
| TGG ATG GCA CCC GAG AGC TTA TTT GAA GGG ATC TAC ACA ATC AAG AGT<br>Trp Met Ala Pro Glu Ser Leu Phe Glu Gly Ile Tyr Thr Ile Lys Ser<br>                  860                        865                        870 | 2646 |
| GAC GTC TGG TCC TAC GGC ATC CTT CTC TGG GAG ATA TTT TCA CTG GGT<br>Asp Val Trp Ser Tyr Gly Ile Leu Leu Trp Glu Ile Phe Ser Leu Gly<br>            875                        880                        885 | 2694 |
| GTG AAC CCT TAC CCT GGC ATT CCT GTC GAC GCT AAC TTC TAT AAA CTG<br>Val Asn Pro Tyr Pro Gly Ile Pro Val Asp Ala Asn Phe Tyr Lys Leu<br>      890                        895                        900 | 2742 |
| ATT CAG AGT GGA TTT AAA ATG GAG CAG CCA TTC TAT GCC ACA GAA GGG<br>Ile Gln Ser Gly Phe Lys Met Glu Gln Pro Phe Tyr Ala Thr Glu Gly<br>905                              910                        915                        920 | 2790 |
| ATA TAC TTT GTA ATG CAA TCC TGC TGG GCT TTT GAC TCA AGG AAG CGG<br>Ile Tyr Phe Val Met Gln Ser Cys Trp Ala Phe Asp Ser Arg Lys Arg<br>                        925                        930                        935 | 2838 |
| CCA TCC TTC CCC AAC CTG ACT TCA TTT TTA GGA TGT CAG CTG GCA GAG<br>Pro Ser Phe Pro Asn Leu Thr Ser Phe Leu Gly Cys Gln Leu Ala Glu<br>                  940                        945                        950 | 2886 |
| GCA GAA GAA GCA TGT ATC AGA ACA TCC ATC CAT CTA CCA AAA CAG GCG<br>Ala Glu Glu Ala Cys Ile Arg Thr Ser Ile His Leu Pro Lys Gln Ala<br>            955                        960                        965 | 2934 |
| GCC CCT CAG CAG AGA GGC GGG CTC AGA GCC CAG TCG CCA CAG CGC CAG<br>Ala Pro Gln Gln Arg Gly Gly Leu Arg Ala Gln Ser Pro Gln Arg Gln<br>970                              975                        980 | 2982 |
| GTG AAG ATT CAC AGA GAA AGA AGT TAGCGAGGAG GCCTTGGACC CCGCCACCCT<br>Val Lys Ile His Arg Glu Arg Ser | 3036 |

|  |  |  |  |  |  |
|---|---|---|---|---|---|
| 985 | | 990 | | | |
| AGCAGGCTGT | AGACCGCAGA | GCCAAGATTA | GCCTCGCCTC | TGAGGAAGCG | CCCTACAGCG | 3096 |
| CGTTGCTTCG | CTGGACTTTT | CTCTAGATGC | TGTCTGCCAT | TACTCCAAAG | TGACTTCTAT | 3156 |
| AAAATCAAAC | CTCTCCTCGC | ACAGGCGGGA | GAGCCAATAA | TGAGACTTGT | TGGTGAGCCC | 3216 |
| GCCTACCCTG | GGGGCCTTTC | CACGAGCTTG | AGGGGAAAGC | CATGTATCTG | AAATATAGTA | 3276 |
| TATTCTTGTA | AATACGTGAA | ACAAACCAAA | CCCGTTTTTT | GCTAAGGGAA | AGCTAAATAT | 3336 |
| GATTTTTAAA | AATCTATGTT | TTAAAATACT | ATGTAACTTT | TCATCTATT | TAGTGATATA | 3396 |
| TTTTATGGAT | GGAAATAAAC | TTTCTACTGT | AAAAAAAAAA | AAAAAAAAAA | AAAAAA | 3453 |

( 2 ) INFORMATION FOR SEQ ID NO:2:

( i ) SEQUENCE CHARACTERISTICS:
( A ) LENGTH: 992 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Arg Ala Leu Ala Gln Arg Ser Asp Arg Arg Leu Leu Leu Leu Val
  1               5                  10                  15
Val Leu Ser Val Met Ile Leu Glu Thr Val Thr Asn Gln Asp Leu Pro
                 20                  25                  30
Val Ile Lys Cys Val Leu Ile Ser His Glu Asn Asn Gly Ser Ser Ala
             35                  40                  45
Gly Lys Pro Ser Ser Tyr Arg Met Val Arg Gly Ser Pro Glu Asp Leu
         50                  55                  60
Gln Cys Thr Pro Arg Arg Gln Ser Glu Gly Thr Val Tyr Glu Ala Ala
 65                  70                  75                  80
Thr Val Glu Val Ala Glu Ser Gly Ser Ile Thr Leu Gln Val Gln Leu
                 85                  90                  95
Ala Thr Pro Gly Asp Leu Ser Cys Leu Trp Val Phe Lys His Ser Ser
                100                 105                 110
Leu Gly Cys Gln Pro His Phe Asp Leu Gln Asn Arg Gly Ile Val Ser
            115                 120                 125
Met Ala Ile Leu Asn Val Thr Glu Thr Gln Ala Gly Glu Tyr Leu Leu
        130                 135                 140
His Ile Gln Ser Glu Arg Ala Asn Tyr Thr Val Leu Phe Thr Val Asn
145                 150                 155                 160
Val Arg Asp Thr Gln Leu Tyr Val Leu Arg Arg Pro Tyr Phe Arg Lys
                165                 170                 175
Met Glu Asn Gln Asp Ala Leu Leu Cys Ile Ser Glu Gly Val Pro Glu
            180                 185                 190
Pro Thr Val Glu Trp Val Leu Cys Ser Ser His Arg Glu Ser Cys Lys
        195                 200                 205
Glu Glu Gly Pro Ala Val Val Arg Lys Glu Glu Lys Val Leu His Glu
    210                 215                 220
Leu Phe Gly Thr Asp Ile Arg Cys Cys Ala Arg Asn Ala Leu Gly Arg
225                 230                 235                 240
Glu Cys Thr Lys Leu Phe Thr Ile Asp Leu Asn Gln Ala Pro Gln Ser
                245                 250                 255
Thr Leu Pro Gln Leu Phe Leu Lys Val Gly Glu Pro Leu Trp Ile Arg
            260                 265                 270
Cys Lys Ala Ile His Val Asn His Gly Phe Gly Leu Thr Trp Glu Leu
        275                 280                 285
```

| | | | | | | | | | | | | | |
|---|---|---|---|---|---|---|---|---|---|---|---|---|---|
| Glu | Asp | Lys | Ala | Leu | Glu | Glu | Gly | Ser | Tyr | Phe | Glu | Met | Ser | Thr | Tyr |
| | 290 | | | | 295 | | | | 300 | | | | | | |
| Ser | Thr | Asn | Arg | Thr | Met | Ile | Arg | Ile | Leu | Leu | Ala | Phe | Val | Ser | Ser |
| 305 | | | | 310 | | | | 315 | | | | | | | 320 |
| Val | Gly | Arg | Asn | Asp | Thr | Gly | Tyr | Tyr | Thr | Cys | Ser | Ser | Ser | Lys | His |
| | | | | 325 | | | | | 330 | | | | | 335 | |
| Pro | Ser | Gln | Ser | Ala | Leu | Val | Thr | Ile | Leu | Glu | Lys | Gly | Phe | Ile | Asn |
| | | | 340 | | | | | 345 | | | | | 350 | | |
| Ala | Thr | Ser | Ser | Gln | Glu | Glu | Tyr | Glu | Ile | Asp | Pro | Tyr | Glu | Lys | Phe |
| | | 355 | | | | | 360 | | | | 365 | | | | |
| Cys | Phe | Ser | Val | Arg | Phe | Lys | Ala | Tyr | Pro | Arg | Ile | Arg | Cys | Thr | Trp |
| | 370 | | | | 375 | | | | | 380 | | | | | |
| Ile | Phe | Ser | Gln | Ala | Ser | Phe | Pro | Cys | Glu | Gln | Arg | Gly | Leu | Glu | Asp |
| 385 | | | | | 390 | | | | | 395 | | | | | 400 |
| Gly | Tyr | Ser | Ile | Ser | Lys | Phe | Cys | Asp | His | Lys | Asn | Lys | Pro | Gly | Glu |
| | | | | 405 | | | | | 410 | | | | | 415 | |
| Tyr | Ile | Phe | Tyr | Ala | Glu | Asn | Asp | Asp | Ala | Gln | Phe | Thr | Lys | Met | Phe |
| | | | 420 | | | | | 425 | | | | | 430 | | |
| Thr | Leu | Asn | Ile | Arg | Lys | Lys | Pro | Gln | Val | Leu | Ala | Asn | Ala | Ser | Ala |
| | | | 435 | | | | 440 | | | | | 445 | | | |
| Ser | Gln | Ala | Ser | Cys | Ser | Ser | Asp | Gly | Tyr | Pro | Leu | Pro | Ser | Trp | Thr |
| | 450 | | | | | 455 | | | | | 460 | | | | |
| Trp | Lys | Lys | Cys | Ser | Asp | Lys | Ser | Pro | Asn | Cys | Thr | Glu | Glu | Ile | Pro |
| 465 | | | | | 470 | | | | | 475 | | | | | 480 |
| Glu | Gly | Val | Trp | Asn | Lys | Lys | Ala | Asn | Arg | Lys | Val | Phe | Gly | Gln | Trp |
| | | | | 485 | | | | | 490 | | | | | 495 | |
| Val | Ser | Ser | Ser | Thr | Leu | Asn | Met | Ser | Glu | Ala | Gly | Lys | Gly | Leu | Leu |
| | | | 500 | | | | | 505 | | | | | 510 | | |
| Val | Lys | Cys | Cys | Ala | Tyr | Asn | Ser | Met | Gly | Thr | Ser | Cys | Glu | Thr | Ile |
| | | 515 | | | | | 520 | | | | | 525 | | | |
| Phe | Leu | Asn | Ser | Pro | Gly | Pro | Phe | Pro | Phe | Ile | Gln | Asp | Asn | Ile | Ser |
| | 530 | | | | 535 | | | | | 540 | | | | | |
| Phe | Tyr | Ala | Thr | Ile | Gly | Leu | Cys | Leu | Pro | Phe | Ile | Val | Val | Leu | Ile |
| 545 | | | | | 550 | | | | 555 | | | | | | 560 |
| Val | Leu | Ile | Cys | His | Lys | Tyr | Lys | Lys | Gln | Phe | Arg | Tyr | Glu | Ser | Gln |
| | | | | 565 | | | | | 570 | | | | | 575 | |
| Leu | Gln | Met | Ile | Gln | Val | Thr | Gly | Pro | Leu | Asp | Asn | Glu | Tyr | Phe | Tyr |
| | | | 580 | | | | | 585 | | | | | 590 | | |
| Val | Asp | Phe | Arg | Asp | Tyr | Glu | Tyr | Asp | Leu | Lys | Trp | Glu | Phe | Pro | Arg |
| | | | 595 | | | | | 600 | | | | 605 | | | |
| Glu | Asn | Leu | Glu | Phe | Gly | Lys | Val | Leu | Gly | Ser | Gly | Ala | Phe | Gly | Arg |
| | 610 | | | | | 615 | | | | | 620 | | | | |
| Val | Met | Asn | Ala | Thr | Ala | Tyr | Gly | Ile | Ser | Lys | Thr | Gly | Val | Ser | Ile |
| 625 | | | | | 630 | | | | | 635 | | | | | 640 |
| Gln | Val | Ala | Val | Lys | Met | Leu | Lys | Glu | Lys | Ala | Asp | Ser | Cys | Glu | Lys |
| | | | | 645 | | | | | 650 | | | | | 655 | |
| Glu | Ala | Leu | Met | Ser | Glu | Leu | Lys | Met | Met | Thr | His | Leu | Gly | His | His |
| | | | 660 | | | | | 665 | | | | | 670 | | |
| Asp | Asn | Ile | Val | Asn | Leu | Leu | Gly | Ala | Cys | Thr | Leu | Ser | Gly | Pro | Val |
| | | 675 | | | | | 680 | | | | | 685 | | | |
| Tyr | Leu | Ile | Phe | Glu | Tyr | Cys | Cys | Tyr | Gly | Asp | Leu | Leu | Asn | Tyr | Leu |
| | 690 | | | | | 695 | | | | | 700 | | | | |
| Arg | Ser | Lys | Arg | Glu | Lys | Phe | His | Arg | Thr | Trp | Thr | Glu | Ile | Phe | Lys |
| 705 | | | | | 710 | | | | | 715 | | | | | 720 |
| Glu | His | Asn | Phe | Ser | Ser | Tyr | Pro | Thr | Phe | Gln | Ala | His | Ser | Asn | Ser |

|     |     |     |     |     | 725 |     |     |     | 730 |     |     |     | 735 |     |
| --- | --- | --- | --- | --- | --- | --- | --- | --- | --- | --- | --- | --- | --- | --- |
| Ser | Met | Pro | Gly | Ser | Arg | Glu | Val | Gln | Leu | His | Pro | Pro | Leu | Asp | Gln |
|     |     |     | 740 |     |     |     |     | 745 |     |     |     | 750 |     |     |
| Leu | Ser | Gly | Phe | Asn | Gly | Asn | Ser | Ile | His | Ser | Glu | Asp | Glu | Ile | Glu |
|     |     | 755 |     |     |     |     | 760 |     |     |     |     | 765 |     |     |
| Tyr | Glu | Asn | Gln | Lys | Arg | Leu | Ala | Glu | Glu | Glu | Glu | Asp | Leu | Asn |
|     | 770 |     |     |     |     | 775 |     |     |     | 780 |     |     |     |     |
| Val | Leu | Thr | Phe | Glu | Asp | Leu | Leu | Cys | Phe | Ala | Tyr | Gln | Val | Ala | Lys |
| 785 |     |     |     |     | 790 |     |     |     |     | 795 |     |     |     |     | 800 |
| Gly | Met | Glu | Phe | Leu | Glu | Phe | Lys | Ser | Cys | Val | His | Arg | Asp | Leu | Ala |
|     |     |     |     | 805 |     |     |     |     | 810 |     |     |     |     | 815 |     |
| Ala | Arg | Asn | Val | Leu | Val | Thr | His | Gly | Lys | Val | Val | Lys | Ile | Cys | Asp |
|     |     |     | 820 |     |     |     |     | 825 |     |     |     |     | 830 |     |     |
| Phe | Gly | Leu | Ala | Arg | Asp | Ile | Leu | Ser | Asp | Ser | Ser | Tyr | Val | Val | Arg |
|     |     | 835 |     |     |     |     | 840 |     |     |     |     | 845 |     |     |     |
| Gly | Asn | Ala | Arg | Leu | Pro | Val | Lys | Trp | Met | Ala | Pro | Glu | Ser | Leu | Phe |
|     | 850 |     |     |     |     | 855 |     |     |     |     | 860 |     |     |     |     |
| Glu | Gly | Ile | Tyr | Thr | Ile | Lys | Ser | Asp | Val | Trp | Ser | Tyr | Gly | Ile | Leu |
| 865 |     |     |     |     | 870 |     |     |     |     | 875 |     |     |     |     | 880 |
| Leu | Trp | Glu | Ile | Phe | Ser | Leu | Gly | Val | Asn | Pro | Tyr | Pro | Gly | Ile | Pro |
|     |     |     |     | 885 |     |     |     |     | 890 |     |     |     |     | 895 |     |
| Val | Asp | Ala | Asn | Phe | Tyr | Lys | Leu | Ile | Gln | Ser | Gly | Phe | Lys | Met | Glu |
|     |     |     | 900 |     |     |     |     | 905 |     |     |     |     | 910 |     |     |
| Gln | Pro | Phe | Tyr | Ala | Thr | Glu | Gly | Ile | Tyr | Phe | Val | Met | Gln | Ser | Cys |
|     |     | 915 |     |     |     |     | 920 |     |     |     |     | 925 |     |     |     |
| Trp | Ala | Phe | Asp | Ser | Arg | Lys | Arg | Pro | Ser | Phe | Pro | Asn | Leu | Thr | Ser |
|     | 930 |     |     |     |     | 935 |     |     |     |     | 940 |     |     |     |     |
| Phe | Leu | Gly | Cys | Gln | Leu | Ala | Glu | Ala | Glu | Ala | Cys | Ile | Arg | Thr |
| 945 |     |     |     |     | 950 |     |     |     |     | 955 |     |     |     |     | 960 |
| Ser | Ile | His | Leu | Pro | Lys | Gln | Ala | Ala | Pro | Gln | Gln | Arg | Gly | Gly | Leu |
|     |     |     |     | 965 |     |     |     |     | 970 |     |     |     |     | 975 |     |
| Arg | Ala | Gln | Ser | Pro | Gln | Arg | Gln | Val | Lys | Ile | His | Arg | Glu | Arg | Ser |
|     |     |     | 980 |     |     |     |     | 985 |     |     |     |     | 990 |     |     |

( 2 ) INFORMATION FOR SEQ ID NO:3:

( i ) SEQUENCE CHARACTERISTICS:
  ( A ) LENGTH: 5406 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 208..4311

( i x ) FEATURE:
  ( A ) NAME/KEY: matpeptide
  ( B ) LOCATION: 208..4308

( x i ) SEQUENCE DESCRIPTION: SEQ ID NO:3:

```
CTGTGTCCCG CAGCCGGATA ACCTGGCTGA CCCGATTCCG CGGACACCCG TGCAGCCGCG      60

GCTGGAGCCA GGGCGCCGGT GCCCGCGCTC TCCCCGGTCT TGCGCTGCGG GGGCCGATAC     120

CGCCTCTGTG ACTTCTTTGC GGGCCAGGGA CGGAGAAGGA GTCTGTGCCT GAGAAACTGG     180

GCTCTGTGCC CAGGCGCGAG GTGCAGG ATG GAG AGC AAG GGC CTG CTA GCT        231
                               Met Glu Ser Lys Gly Leu Leu Ala
                                1               5
```

| | | | | | | | | | | | | | | | | |
|---|---|---|---|---|---|---|---|---|---|---|---|---|---|---|---|---|
| GTC | GCT | CTG | TGG | TTC | TGC | GTG | GAG | ACC | CGA | GCC | GCC | TCT | GTG | GGT | TTG | 279 |
| Val | Ala | Leu | Trp | Phe | Cys | Val | Glu | Thr | Arg | Ala | Ala | Ser | Val | Gly | Leu | |
| | 10 | | | | 15 | | | | | 20 | | | | | | |
| CCT | GGC | GAT | TTT | CTC | CAT | CCC | CCC | AAG | CTC | AGC | ACA | CAG | AAA | GAC | ATA | 327 |
| Pro | Gly | Asp | Phe | Leu | His | Pro | Pro | Lys | Leu | Ser | Thr | Gln | Lys | Asp | Ile | |
| 25 | | | | | 30 | | | | | 35 | | | | | 40 | |
| CTG | ACA | ATT | TTG | GCA | AAT | ACA | ACC | CTT | CAG | ATT | ACT | TGC | AGG | GGA | CAG | 375 |
| Leu | Thr | Ile | Leu | Ala | Asn | Thr | Thr | Leu | Gln | Ile | Thr | Cys | Arg | Gly | Gln | |
| | | | | 45 | | | | | 50 | | | | | 55 | | |
| CGG | GAC | CTG | GAC | TGG | CTT | TGG | CCC | AAT | GCT | CAG | CGT | GAT | TCT | GAG | GAA | 423 |
| Arg | Asp | Leu | Asp | Trp | Leu | Trp | Pro | Asn | Ala | Gln | Arg | Asp | Ser | Glu | Glu | |
| | | | 60 | | | | | 65 | | | | | 70 | | | |
| AGG | GTA | TTG | GTG | ACT | GAA | TGC | GGC | GGT | GGT | GAC | AGT | ATC | TTC | TGC | AAA | 471 |
| Arg | Val | Leu | Val | Thr | Glu | Cys | Gly | Gly | Gly | Asp | Ser | Ile | Phe | Cys | Lys | |
| | | 75 | | | | | 80 | | | | | 85 | | | | |
| ACA | CTC | ACC | ATT | CCC | AGG | GTG | GTT | GGA | AAT | GAT | ACT | GGA | GCC | TAC | AAG | 519 |
| Thr | Leu | Thr | Ile | Pro | Arg | Val | Val | Gly | Asn | Asp | Thr | Gly | Ala | Tyr | Lys | |
| | 90 | | | | | 95 | | | | | 100 | | | | | |
| TGC | TCG | TAC | CGG | GAC | GTC | GAC | ATA | GCC | TCC | ACT | GTT | TAT | GTC | TAT | GTT | 567 |
| Cys | Ser | Tyr | Arg | Asp | Val | Asp | Ile | Ala | Ser | Thr | Val | Tyr | Val | Tyr | Val | |
| 105 | | | | | 110 | | | | | 115 | | | | | 120 | |
| CGA | GAT | TAC | AGA | TCA | CCA | TTC | ATC | GCC | TCT | GTC | AGT | GAC | CAG | CAT | GGC | 615 |
| Arg | Asp | Tyr | Arg | Ser | Pro | Phe | Ile | Ala | Ser | Val | Ser | Asp | Gln | His | Gly | |
| | | | | 125 | | | | | 130 | | | | | 135 | | |
| ATC | GTG | TAC | ATC | ACC | GAG | AAC | AAG | AAC | AAA | ACT | GTG | GTG | ATC | CCC | TGC | 663 |
| Ile | Val | Tyr | Ile | Thr | Glu | Asn | Lys | Asn | Lys | Thr | Val | Val | Ile | Pro | Cys | |
| | | | 140 | | | | | 145 | | | | | 150 | | | |
| CGA | GGG | TCG | ATT | TCA | AAC | CTC | AAT | GTG | TCT | CTT | TGC | GCT | AGG | TAT | CCA | 711 |
| Arg | Gly | Ser | Ile | Ser | Asn | Leu | Asn | Val | Ser | Leu | Cys | Ala | Arg | Tyr | Pro | |
| | | 155 | | | | | 160 | | | | | 165 | | | | |
| GAA | AAG | AGA | TTT | GTT | CCG | GAT | GGA | AAC | AGA | ATT | TCC | TGG | GAC | AGC | GAG | 759 |
| Glu | Lys | Arg | Phe | Val | Pro | Asp | Gly | Asn | Arg | Ile | Ser | Trp | Asp | Ser | Glu | |
| | 170 | | | | | 175 | | | | | 180 | | | | | |
| ATA | GGC | TTT | ACT | CTC | CCC | AGT | TAC | ATG | ATC | AGC | TAT | GCC | GGC | ATG | GTC | 807 |
| Ile | Gly | Phe | Thr | Leu | Pro | Ser | Tyr | Met | Ile | Ser | Tyr | Ala | Gly | Met | Val | |
| 185 | | | | | 190 | | | | | 195 | | | | | 200 | |
| TTC | TGT | GAG | GCA | AAG | ATC | AAT | GAT | GAA | ACC | TAT | CAG | TCT | ATC | ATG | TAC | 855 |
| Phe | Cys | Glu | Ala | Lys | Ile | Asn | Asp | Glu | Thr | Tyr | Gln | Ser | Ile | Met | Tyr | |
| | | | | 205 | | | | | 210 | | | | | 215 | | |
| ATA | GTT | GTG | GTT | GTA | GGA | TAT | AGG | ATT | TAT | GAT | GTG | ATT | CTG | AGC | CCC | 903 |
| Ile | Val | Val | Val | Val | Gly | Tyr | Arg | Ile | Tyr | Asp | Val | Ile | Leu | Ser | Pro | |
| | | | 220 | | | | | 225 | | | | | 230 | | | |
| CCG | CAT | GAA | ATT | GAG | CTA | TCT | GCC | GGA | GAA | AAA | CTT | GTC | TTA | AAT | TGT | 951 |
| Pro | His | Glu | Ile | Glu | Leu | Ser | Ala | Gly | Glu | Lys | Leu | Val | Leu | Asn | Cys | |
| | | 235 | | | | | 240 | | | | | 245 | | | | |
| ACA | GCG | AGA | ACA | GAG | CTC | AAT | GTG | GGG | CTT | GAT | TTC | ACC | TGG | CAC | TCT | 999 |
| Thr | Ala | Arg | Thr | Glu | Leu | Asn | Val | Gly | Leu | Asp | Phe | Thr | Trp | His | Ser | |
| | 250 | | | | | 255 | | | | | 260 | | | | | |
| CCA | CCT | TCA | AAG | TCT | CAT | CAT | AAG | AAG | ATT | GTA | AAC | CGG | GAT | GTG | AAA | 1047 |
| Pro | Pro | Ser | Lys | Ser | His | His | Lys | Lys | Ile | Val | Asn | Arg | Asp | Val | Lys | |
| 265 | | | | | 270 | | | | | 275 | | | | | 280 | |
| CCC | TTT | CCT | GGG | ACT | GTG | GCG | AAG | ATG | TTT | TTG | AGC | ACC | TTG | ACA | ATA | 1095 |
| Pro | Phe | Pro | Gly | Thr | Val | Ala | Lys | Met | Phe | Leu | Ser | Thr | Leu | Thr | Ile | |
| | | | | 285 | | | | | 290 | | | | | 295 | | |
| GAA | AGT | GTG | ACC | AAG | AGT | GAC | CAA | GGG | GAA | TAC | ACC | TGT | GTA | GCG | TCC | 1143 |
| Glu | Ser | Val | Thr | Lys | Ser | Asp | Gln | Gly | Glu | Tyr | Thr | Cys | Val | Ala | Ser | |
| | | | 300 | | | | | 305 | | | | | 310 | | | |
| AGT | GGA | CGG | ATG | ATC | AAG | AGA | AAT | AGA | ACA | TTT | GTC | CGA | GTT | CAC | ACA | 1191 |
| Ser | Gly | Arg | Met | Ile | Lys | Arg | Asn | Arg | Thr | Phe | Val | Arg | Val | His | Thr | |
| | | 315 | | | | | 320 | | | | | 325 | | | | |
| AAG | CCT | TTT | ATT | GCT | TTC | GGT | AGT | GGG | ATG | AAA | TCT | TTG | GTG | GAA | GCC | 1239 |
| Lys | Pro | Phe | Ile | Ala | Phe | Gly | Ser | Gly | Met | Lys | Ser | Leu | Val | Glu | Ala | |

-continued

```
              330                         335                         340
ACA GTG GGC AGT CAA GTC CGA ATC CCT GTG AAG TAT CTC AGT TAC CCA              1287
Thr Val Gly Ser Gln Val Arg Ile Pro Val Lys Tyr Leu Ser Tyr Pro
345                 350                 355                 360

GCT CCT GAT ATC AAA TGG TAC AGA AAT GGA AGG CCC ATT GAG TCC AAC              1335
Ala Pro Asp Ile Lys Trp Tyr Arg Asn Gly Arg Pro Ile Glu Ser Asn
                        365                 370                 375

TAC ACA ATG ATT GTT GGC GAT GAA CTC ACC ATC ATG GAA GTG ACT GAA              1383
Tyr Thr Met Ile Val Gly Asp Glu Leu Thr Ile Met Glu Val Thr Glu
            380                 385                 390

AGA GAT GCA GGA AAC TAC ACG GTC ATC CTC ACC AAC CCC ATT TCA ATG              1431
Arg Asp Ala Gly Asn Tyr Thr Val Ile Leu Thr Asn Pro Ile Ser Met
        395                 400                 405

GAG AAA CAG AGC CAC ATG GTC TCT CTG GTT GTG AAT GTC CCA CCC CAG              1479
Glu Lys Gln Ser His Met Val Ser Leu Val Val Asn Val Pro Pro Gln
410                 415                 420

ATC GGT GAG AAA GCC TTG ATC TCG CCT ATG GAT TCC TAC CAG TAT GGG              1527
Ile Gly Glu Lys Ala Leu Ile Ser Pro Met Asp Ser Tyr Gln Tyr Gly
425                 430                 435                 440

ACC ATG CAG ACA TTG ACA TGC ACA GTC TAC GCC AAC CCT CCC CTG CAC              1575
Thr Met Gln Thr Leu Thr Cys Thr Val Tyr Ala Asn Pro Pro Leu His
                        445                 450                 455

CAC ATC CAG TGG TAC TGG CAG CTA GAA GAA GCC TGC TCC TAC AGA CCC              1623
His Ile Gln Trp Tyr Trp Gln Leu Glu Glu Ala Cys Ser Tyr Arg Pro
            460                 465                 470

GGC CAA ACA AGC CCG TAT GCT TGT AAA GAA TGG AGA CAC GTG GAG GAT              1671
Gly Gln Thr Ser Pro Tyr Ala Cys Lys Glu Trp Arg His Val Glu Asp
        475                 480                 485

TTC CAG GGG GGA AAC AAG ATC GAA GTC ACC AAA AAC CAA TAT GCC CTG              1719
Phe Gln Gly Gly Asn Lys Ile Glu Val Thr Lys Asn Gln Tyr Ala Leu
490                 495                 500

ATT GAA GGA AAA AAC AAA ACT GTA AGT ACG CTG GTC ATC CAA GCT GCC              1767
Ile Glu Gly Lys Asn Lys Thr Val Ser Thr Leu Val Ile Gln Ala Ala
505                 510                 515                 520

AAC GTG TCA GCG TTG TAC AAA TGT GAA GCC ATC AAC AAA GCG GGA CGA              1815
Asn Val Ser Ala Leu Tyr Lys Cys Glu Ala Ile Asn Lys Ala Gly Arg
                        525                 530                 535

GGA GAG AGG GTC ATC TCC TTC CAT GTG ATC AGG GGT CCT GAA ATT ACT              1863
Gly Glu Arg Val Ile Ser Phe His Val Ile Arg Gly Pro Glu Ile Thr
            540                 545                 550

GTG CAA CCT GCT GCC CAG CCA ACT GAG CAG GAG AGT GTG TCC CTG TTG              1911
Val Gln Pro Ala Ala Gln Pro Thr Glu Gln Glu Ser Val Ser Leu Leu
        555                 560                 565

TGC ACT GCA GAC AGA AAT ACG TTT GAG AAC CTC ACG TGG TAC AAG CTT              1959
Cys Thr Ala Asp Arg Asn Thr Phe Glu Asn Leu Thr Trp Tyr Lys Leu
570                 575                 580

GGC TCA CAG GCA ACA TCG GTC CAC ATG GGC GAA TCA CTC ACA CCA GTT              2007
Gly Ser Gln Ala Thr Ser Val His Met Gly Glu Ser Leu Thr Pro Val
585                 590                 595                 600

TGC AAG AAC TTG GAT GCT CTT TGG AAA CTG AAT GGC ACC ATG TTT TCT              2055
Cys Lys Asn Leu Asp Ala Leu Trp Lys Leu Asn Gly Thr Met Phe Ser
                        605                 610                 615

AAC AGC ACA AAT GAC ATC TTG ATT GTG GCA TTT CAG AAT GCC TCT CTG              2103
Asn Ser Thr Asn Asp Ile Leu Ile Val Ala Phe Gln Asn Ala Ser Leu
            620                 625                 630

CAG GAC CAA GGC GAC TAT GTT TGC TCT GCT CAA GAT AAG AAG ACC AAG              2151
Gln Asp Gln Gly Asp Tyr Val Cys Ser Ala Gln Asp Lys Lys Thr Lys
        635                 640                 645

AAA AGA CAT TGC CTG GTC AAA CAG CTC ATC ATC CTA GAG CGC ATG GCA              2199
Lys Arg His Cys Leu Val Lys Gln Leu Ile Ile Leu Glu Arg Met Ala
650                 655                 660
```

```
CCC  ATG  ATC  ACC  GGA  AAT  CTG  GAG  AAT  CAG  ACA  ACA  ACC  ATT  GGC  GAG      2247
Pro  Met  Ile  Thr  Gly  Asn  Leu  Glu  Asn  Gln  Thr  Thr  Thr  Ile  Gly  Glu
665            670                 675                           680

ACC  ATT  GAA  GTG  ACT  TGC  CCA  GCA  TCT  GGA  AAT  CCT  ACC  CCA  CAC  ATT      2295
Thr  Ile  Glu  Val  Thr  Cys  Pro  Ala  Ser  Gly  Asn  Pro  Thr  Pro  His  Ile
               685                      690                      695

ACA  TGG  TTC  AAA  GAC  AAC  GAG  ACC  CTG  GTA  GAA  GAT  TCA  GGC  ATT  GTA      2343
Thr  Trp  Phe  Lys  Asp  Asn  Glu  Thr  Leu  Val  Glu  Asp  Ser  Gly  Ile  Val
                    700                 705                      710

CTG  AGA  GAT  GGG  AAC  CGG  AAC  CTG  ACT  ATC  CGC  AGG  GTG  AGG  AAG  GAG      2391
Leu  Arg  Asp  Gly  Asn  Arg  Asn  Leu  Thr  Ile  Arg  Arg  Val  Arg  Lys  Glu
          715                 720                      725

GAT  GGA  GGC  CTC  TAC  ACC  TGC  CAG  GCC  TGC  AAT  GTC  CTT  GGC  TGT  GCA      2439
Asp  Gly  Gly  Leu  Tyr  Thr  Cys  Gln  Ala  Cys  Asn  Val  Leu  Gly  Cys  Ala
          730                 735                 740

AGA  GCG  GAG  ACG  CTC  TTC  ATA  ATA  GAA  GGT  GCC  CAG  GAA  AAG  ACC  AAC      2487
Arg  Ala  Glu  Thr  Leu  Phe  Ile  Ile  Glu  Gly  Ala  Gln  Glu  Lys  Thr  Asn
745                      750                 755                      760

TTG  GAA  GTC  ATT  ATC  CTC  GTC  GGC  ACT  GCA  GTG  ATT  GCC  ATG  TTC  TTC      2535
Leu  Glu  Val  Ile  Ile  Leu  Val  Gly  Thr  Ala  Val  Ile  Ala  Met  Phe  Phe
                    765                 770                      775

TGG  CTC  CTT  CTT  GTC  ATT  CTC  GTA  CGG  ACC  GTT  AAG  CGG  GCC  AAT  GAA      2583
Trp  Leu  Leu  Leu  Val  Ile  Leu  Val  Arg  Thr  Val  Lys  Arg  Ala  Asn  Glu
                    780                 785                      790

GGG  GAA  CTG  AAG  ACA  GGC  TAC  TTG  TCT  ATT  GTC  ATG  GAT  CCA  GAT  GAA      2631
Gly  Glu  Leu  Lys  Thr  Gly  Tyr  Leu  Ser  Ile  Val  Met  Asp  Pro  Asp  Glu
          795                 800                      805

TTG  CCC  TTG  GAT  GAG  CGC  TGT  GAA  CGC  TTG  CCT  TAT  GAT  GCC  AGC  AAG      2679
Leu  Pro  Leu  Asp  Glu  Arg  Cys  Glu  Arg  Leu  Pro  Tyr  Asp  Ala  Ser  Lys
810                      815                 820

TGG  GAA  TTC  CCC  AGG  GAC  CGG  CTG  AAA  CTA  GGA  AAA  CCT  CTT  GGC  CGC      2727
Trp  Glu  Phe  Pro  Arg  Asp  Arg  Leu  Lys  Leu  Gly  Lys  Pro  Leu  Gly  Arg
825                      830                      835                      840

GGT  GCC  TTC  GGC  CAA  GTG  ATT  GAG  GCA  GAC  GCT  TTT  GGA  ATT  GAC  AAG      2775
Gly  Ala  Phe  Gly  Gln  Val  Ile  Glu  Ala  Asp  Ala  Phe  Gly  Ile  Asp  Lys
               845                      850                      855

ACA  GCG  ACT  TGC  AAA  ACA  GTA  GCC  GTC  AAG  ATG  TTG  AAA  GAA  GGA  GCA      2823
Thr  Ala  Thr  Cys  Lys  Thr  Val  Ala  Val  Lys  Met  Leu  Lys  Glu  Gly  Ala
               860                      865                      870

ACA  CAC  AGC  GAG  CAT  CGA  GCC  CTC  ATG  TCT  GAA  CTC  AAG  ATC  CTC  ATC      2871
Thr  His  Ser  Glu  His  Arg  Ala  Leu  Met  Ser  Glu  Leu  Lys  Ile  Leu  Ile
          875                      880                      885

CAC  ATT  GGT  CAC  CAT  CTC  AAT  GTG  GTG  AAC  CTC  CTA  GGC  GCC  TGC  ACC      2919
His  Ile  Gly  His  His  Leu  Asn  Val  Val  Asn  Leu  Leu  Gly  Ala  Cys  Thr
890                      895                      900

AAG  CCG  GGA  GGG  CCT  CTC  ATG  GTG  ATT  GTG  GAA  TTC  TCG  AAG  TTT  GGA      2967
Lys  Pro  Gly  Gly  Pro  Leu  Met  Val  Ile  Val  Glu  Phe  Ser  Lys  Phe  Gly
905                      910                      915                      920

AAC  CTA  TCA  ACT  TAC  TTA  CGG  GGC  AAG  AGA  AAT  GAA  TTT  GTT  CCC  TAT      3015
Asn  Leu  Ser  Thr  Tyr  Leu  Arg  Gly  Lys  Arg  Asn  Glu  Phe  Val  Pro  Tyr
                    925                 930                      935

AAG  AGC  AAA  GGG  GCA  CGC  TTC  CGC  CAG  GGC  AAG  GAC  TAC  GTT  GGG  GAG      3063
Lys  Ser  Lys  Gly  Ala  Arg  Phe  Arg  Gln  Gly  Lys  Asp  Tyr  Val  Gly  Glu
               940                      945                      950

CTC  TCC  GTG  GAT  CTG  AAA  AGA  CGC  TTG  GAC  AGC  ATC  ACC  AGC  AGC  CAG      3111
Leu  Ser  Val  Asp  Leu  Lys  Arg  Arg  Leu  Asp  Ser  Ile  Thr  Ser  Ser  Gln
          955                      960                      965

AGC  TCT  GCC  AGC  TCA  GGC  TTT  GTT  GAG  GAG  AAA  TCG  CTC  AGT  GAT  GTA      3159
Ser  Ser  Ala  Ser  Ser  Gly  Phe  Val  Glu  Glu  Lys  Ser  Leu  Ser  Asp  Val
970                      975                      980

GAG  GAA  GAA  GAA  GCT  TCT  GAA  GAA  CTG  TAC  AAG  GAC  TTC  CTG  ACC  TTG      3207
Glu  Glu  Glu  Glu  Ala  Ser  Glu  Glu  Leu  Tyr  Lys  Asp  Phe  Leu  Thr  Leu
```

|  |  |  |  |  |  |  |  |  |  |  |  |  |  |  |  |
|---|---|---|---|---|---|---|---|---|---|---|---|---|---|---|---|
| 985 |  |  |  |  | 990 |  |  |  |  | 995 |  |  |  |  | 1000 |

```
GAG CAT CTC ATC TGT TAC AGC TTC CAA GTG GCT AAG GGC ATG GAG TTC     3255
Glu His Leu Ile Cys Tyr Ser Phe Gln Val Ala Lys Gly Met Glu Phe
             1005                1010                1015

TTG GCA TCA AGG AAG TGT ATC CAC AGG GAC CTG GCA GCA CGA AAC ATT     3303
Leu Ala Ser Arg Lys Cys Ile His Arg Asp Leu Ala Ala Arg Asn Ile
         1020                1025                1030

CTC CTA TCG GAG AAG AAT GTG GTT AAG ATC TGT GAC TTC GGC TTG GCC     3351
Leu Leu Ser Glu Lys Asn Val Val Lys Ile Cys Asp Phe Gly Leu Ala
         1035                1040                1045

CGG GAC ATT TAT AAA GAC CCG GAT TAT GTC AGA AAA GGA GAT GCC CGA     3399
Arg Asp Ile Tyr Lys Asp Pro Asp Tyr Val Arg Lys Gly Asp Ala Arg
         1050                1055                1060

CTC CCT TTG AAG TGG ATG GCC CCG GAA ACC ATT TTT GAC AGA GTA TAC     3447
Leu Pro Leu Lys Trp Met Ala Pro Glu Thr Ile Phe Asp Arg Val Tyr
1065                1070                1075                1080

ACA ATT CAG AGC GAT GTG TGG TCT TTC GGT GTG TTG CTC TGG GAA ATA     3495
Thr Ile Gln Ser Asp Val Trp Ser Phe Gly Val Leu Leu Trp Glu Ile
             1085                1090                1095

TTT TCC TTA GGT GCC TCC CCA TAC CCT GGG GTC AAG ATT GAT GAA GAA     3543
Phe Ser Leu Gly Ala Ser Pro Tyr Pro Gly Val Lys Ile Asp Glu Glu
             1100                1105                1110

TTT TGT AGG AGA TTG AAA GAA GGA ACT AGA ATG CGG GCT CCT GAC TAC     3591
Phe Cys Arg Arg Leu Lys Glu Gly Thr Arg Met Arg Ala Pro Asp Tyr
             1115                1120                1125

ACT ACC CCA GAA ATG TAC CAG ACC ATG CTG GAC TGC TGG CAT GAG GAC     3639
Thr Thr Pro Glu Met Tyr Gln Thr Met Leu Asp Cys Trp His Glu Asp
         1130                1135                1140

CCC AAC CAG AGA CCC TCG TTT TCA GAG TTG GTG GAG CAT TTG GGA AAC     3687
Pro Asn Gln Arg Pro Ser Phe Ser Glu Leu Val Glu His Leu Gly Asn
1145                1150                1155                1160

CTC CTG CAA GCA AAT GCG CAG CAG GAT GGC AAA GAC TAT ATT GTT CTT     3735
Leu Leu Gln Ala Asn Ala Gln Gln Asp Gly Lys Asp Tyr Ile Val Leu
             1165                1170                1175

CCA ATG TCA GAG ACA CTG AGC ATG GAA GAG GAT TCT GGA CTC TCC CTG     3783
Pro Met Ser Glu Thr Leu Ser Met Glu Glu Asp Ser Gly Leu Ser Leu
             1180                1185                1190

CCT ACC TCA CCT GTT TCC TGT ATG GAG GAA GAG GAA GTG TGC GAC CCC     3831
Pro Thr Ser Pro Val Ser Cys Met Glu Glu Glu Glu Val Cys Asp Pro
             1195                1200                1205

AAA TTC CAT TAT GAC AAC ACA GCA GGA ATC AGT CAT TAT CTC CAG AAC     3879
Lys Phe His Tyr Asp Asn Thr Ala Gly Ile Ser His Tyr Leu Gln Asn
         1210                1215                1220

AGT AAG CGA AAG AGC CGG CCA GTG AGT GTA AAA ACA TTT GAA GAT ATC     3927
Ser Lys Arg Lys Ser Arg Pro Val Ser Val Lys Thr Phe Glu Asp Ile
1225                1230                1235                1240

CCA TTG GAG GAA CCA GAA GTA AAA GTG ATC CCA GAT GAC AGC CAG ACA     3975
Pro Leu Glu Glu Pro Glu Val Lys Val Ile Pro Asp Asp Ser Gln Thr
             1245                1250                1255

GAC AGT GGG ATG GTC CTT GCA TCA GAA GAG CTG AAA ACT CTG GAA GAC     4023
Asp Ser Gly Met Val Leu Ala Ser Glu Glu Leu Lys Thr Leu Glu Asp
         1260                1265                1270

AGG AAC AAA TTA TCT CCA TCT TTT GGT GGA ATG ATG CCC AGT AAA AGC     4071
Arg Asn Lys Leu Ser Pro Ser Phe Gly Gly Met Met Pro Ser Lys Ser
         1275                1280                1285

AGG GAG TCT GTG GCC TCG GAA GGC TCC AAC CAG ACC AGT GGC TAC CAG     4119
Arg Glu Ser Val Ala Ser Glu Gly Ser Asn Gln Thr Ser Gly Tyr Gln
         1290                1295                1300

TCT GGG TAT CAC TCA GAT GAC ACA GAC ACC ACC GTG TAC TCC AGC GAC     4167
Ser Gly Tyr His Ser Asp Asp Thr Asp Thr Thr Val Tyr Ser Ser Asp
1305                1310                1315                1320
```

| | | | | | | | | | | | | | | | | |
|---|---|---|---|---|---|---|---|---|---|---|---|---|---|---|---|---|
| GAG | GCA | GGA | CTT | TTA | AAG | ATG | GTG | GAT | GCT | GCA | GTT | CAC | GCT | GAC | TCA | 4215 |
| Glu | Ala | Gly | Leu | Leu | Lys | Met | Val | Asp | Ala | Ala | Val | His | Ala | Asp | Ser | |
| | | | | 1325 | | | | 1330 | | | | | | 1335 | | |
| GGG | ACC | ACA | CTG | CAG | CTC | ACC | TCC | TGT | TTA | AAT | GGA | AGT | GGT | CCT | GTC | 4263 |
| Gly | Thr | Thr | Leu | Gln | Leu | Thr | Ser | Cys | Leu | Asn | Gly | Ser | Gly | Pro | Val | |
| | | | 1340 | | | | 1345 | | | | | 1350 | | | | |
| CCG | GCT | CCG | CCC | CCA | ACT | CCT | GGA | AAT | CAC | GAG | AGA | GGT | GCT | GCT | TAGATTTT | 4318 |
| Pro | Ala | Pro | Pro | Pro | Thr | Pro | Gly | Asn | His | Glu | Arg | Gly | Ala | Ala | | |
| | | 1355 | | | | | 1360 | | | | | 1365 | | | | |

```
AGTGTTGTTC TTTCCACCAC CCGGAAGTAG CCACATTTGA TTTTCATTTT TGGAGGAGGG    4378
ACCTCAGACT GCAAGGAGCT TGTCCTCAGG GCATTTCCAG AGAAGATGCC CATGACCCAA    4438
GAATGTGTTG ACTCTACTCT CTTTTCCATT CATTTAAAAG TCCTATATAA TGTGCCCTGC    4498
TGTGGTCTCA CTACCAGTTA AAGCAAAAGA CTTTCAAACA CGTGGACTCT GTCCTCCAAG    4558
AAGTGGCAAC GGCACCTCTG TGAAACTGGA TCGAATGGGC AATGCTTTGT GTGTTGAGGA    4618
TGGGTGAGAT GTCCCAGGGC CGAGTCTGTC TACCTTGGAG GCTTTGTGGA GGATGCGGCT    4678
ATGAGCCAAG TGTTAAGTGT GGGATGTGGA CTGGGAGGAA GGAAGGCGCA AGCCGTCCGG    4738
AGAGCGGTTG GAGCCTGCAG ATGCATTGTG CTGGCTCTGG TGAGGTGGG CTTGTGGCCT    4798
GTCAGGAAAC GCAAAGGCGG CCGGCAGGGT TTGGTTTTGG AAGGTTTGCG TGCTCTTCAC    4858
AGTCGGGTTA CAGGCGAGTT CCCTGTGGCG TTTCCTACTC CTAATGAGAG TTCCTTCCGG    4918
ACTCTTACGT GTCTCCTGGC CTGGCCCCAG GAAGGAAATG ATGCAGCTTG CTCCTTCCTC    4978
ATCTCTCAGG CTGTGCCTTA ATTCAGAACA CCAAAAGAGA GGAACGTCGG CAGAGGCTCC    5038
TGACGGGGCC GAAGAATTGT GAGAACAGAA CAGAAACTCA GGGTTTCTGC TGGGTGGAGA    5098
CCCACGTGGC GCCCTGGTGG CAGGTCTGAG GGTTCTCTGT CAAGTGGCGG TAAAGGCTCA    5158
GGCTGGTGTT CTTCCTCTAT CTCCACTCCT GTCAGGCCCC CAAGTCCTCA GTATTTAGC    5218
TTTGTGGCTT CCTGATGGCA GAAAAATCTT AATTGGTTGG TTTGCTCTCC AGATAATCAC    5278
TAGCCAGATT TCGAAATTAC TTTTTAGCCG AGGTTATGAT AACATCTACT GTATCCTTTA    5338
GAATTTTAAC CTATAAAACT ATGTCTACTG GTTTCTGCCT GTGTGCTTAT GTTAAAAAAA    5398
AAAAAAAA                                                            5406
```

( 2 ) INFORMATION FOR SEQ ID NO:4:

( i ) SEQUENCE CHARACTERISTICS:
        ( A ) LENGTH: 1367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Glu Ser Lys Gly Leu Leu Ala Val Ala Leu Trp Phe Cys Val Glu
 1               5                  10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110
```

-continued

| | | | | | | | | | | | | |
|---|---|---|---|---|---|---|---|---|---|---|---|---|
| Ala | Ser | Thr | Val | Tyr | Val | Tyr | Val | Arg | Asp | Tyr | Arg | Ser | Pro | Phe | Ile |
| | | 115 | | | 120 | | | | | 125 | | |
| Ala | Ser | Val | Ser | Asp | Gln | His | Gly | Ile | Val | Tyr | Ile | Thr | Glu | Asn | Lys |
| | 130 | | | | 135 | | | | 140 | | |
| Asn | Lys | Thr | Val | Val | Ile | Pro | Cys | Arg | Gly | Ser | Ile | Ser | Asn | Leu | Asn |
| 145 | | | | | 150 | | | | 155 | | | | 160 |
| Val | Ser | Leu | Cys | Ala | Arg | Tyr | Pro | Glu | Lys | Arg | Phe | Val | Pro | Asp | Gly |
| | | | 165 | | | | | 170 | | | | | 175 |
| Asn | Arg | Ile | Ser | Trp | Asp | Ser | Glu | Ile | Gly | Phe | Thr | Leu | Pro | Ser | Tyr |
| | | | 180 | | | | 185 | | | | 190 | | |
| Met | Ile | Ser | Tyr | Ala | Gly | Met | Val | Phe | Cys | Glu | Ala | Lys | Ile | Asn | Asp |
| | | 195 | | | | 200 | | | | 205 | | |
| Glu | Thr | Tyr | Gln | Ser | Ile | Met | Tyr | Ile | Val | Val | Val | Gly | Tyr | Arg |
| | 210 | | | | 215 | | | | 220 | | |
| Ile | Tyr | Asp | Val | Ile | Leu | Ser | Pro | Pro | His | Glu | Ile | Glu | Leu | Ser | Ala |
| 225 | | | | 230 | | | | 235 | | | | 240 |
| Gly | Glu | Lys | Leu | Val | Leu | Asn | Cys | Thr | Ala | Arg | Thr | Glu | Leu | Asn | Val |
| | | | 245 | | | | 250 | | | | 255 |
| Gly | Leu | Asp | Phe | Thr | Trp | His | Ser | Pro | Pro | Ser | Lys | Ser | His | His | Lys |
| | | 260 | | | | 265 | | | | 270 | | |
| Lys | Ile | Val | Asn | Arg | Asp | Val | Lys | Pro | Phe | Pro | Gly | Thr | Val | Ala | Lys |
| | | 275 | | | | 280 | | | | 285 |
| Met | Phe | Leu | Ser | Thr | Leu | Thr | Ile | Glu | Ser | Val | Thr | Lys | Ser | Asp | Gln |
| | 290 | | | | 295 | | | | 300 | | |
| Gly | Glu | Tyr | Thr | Cys | Val | Ala | Ser | Ser | Gly | Arg | Met | Ile | Lys | Arg | Asn |
| 305 | | | | 310 | | | | 315 | | | | 320 |
| Arg | Thr | Phe | Val | Arg | Val | His | Thr | Lys | Pro | Phe | Ile | Ala | Phe | Gly | Ser |
| | | | 325 | | | | 330 | | | | 335 |
| Gly | Met | Lys | Ser | Leu | Val | Glu | Ala | Thr | Val | Gly | Ser | Gln | Val | Arg | Ile |
| | | 340 | | | | 345 | | | | 350 |
| Pro | Val | Lys | Tyr | Leu | Ser | Tyr | Pro | Ala | Pro | Asp | Ile | Lys | Trp | Tyr | Arg |
| | | 355 | | | | 360 | | | | 365 |
| Asn | Gly | Arg | Pro | Ile | Glu | Ser | Asn | Tyr | Thr | Met | Ile | Val | Gly | Asp | Glu |
| | 370 | | | | 375 | | | | 380 |
| Leu | Thr | Ile | Met | Glu | Val | Thr | Glu | Arg | Asp | Ala | Gly | Asn | Tyr | Thr | Val |
| 385 | | | | 390 | | | | 395 | | | | 400 |
| Ile | Leu | Thr | Asn | Pro | Ile | Ser | Met | Glu | Lys | Gln | Ser | His | Met | Val | Ser |
| | | | 405 | | | | 410 | | | | 415 |
| Leu | Val | Val | Asn | Val | Pro | Pro | Gln | Ile | Gly | Glu | Lys | Ala | Leu | Ile | Ser |
| | | | 420 | | | | 425 | | | | 430 |
| Pro | Met | Asp | Ser | Tyr | Gln | Tyr | Gly | Thr | Met | Gln | Thr | Leu | Thr | Cys | Thr |
| | | 435 | | | | 440 | | | | 445 |
| Val | Tyr | Ala | Asn | Pro | Pro | Leu | His | His | Ile | Gln | Trp | Tyr | Trp | Gln | Leu |
| 450 | | | | | 455 | | | | 460 | | |
| Glu | Glu | Ala | Cys | Ser | Tyr | Arg | Pro | Gly | Gln | Thr | Ser | Pro | Tyr | Ala | Cys |
| 465 | | | | | 470 | | | | 475 | | | | 480 |
| Lys | Glu | Trp | Arg | His | Val | Glu | Asp | Phe | Gln | Gly | Gly | Asn | Lys | Ile | Glu |
| | | | | 485 | | | | 490 | | | | 495 |
| Val | Thr | Lys | Asn | Gln | Tyr | Ala | Leu | Ile | Glu | Gly | Lys | Asn | Lys | Thr | Val |
| | | | 500 | | | | 505 | | | | 510 |
| Ser | Thr | Leu | Val | Ile | Gln | Ala | Ala | Asn | Val | Ser | Ala | Leu | Tyr | Lys | Cys |
| | | | 515 | | | | 520 | | | | 525 |
| Glu | Ala | Ile | Asn | Lys | Ala | Gly | Arg | Gly | Glu | Arg | Val | Ile | Ser | Phe | His |
| | | 530 | | | | 535 | | | | 540 |

|   |   |   |   |   |   |   |   |   |   |   |   |   |   |   |
|---|---|---|---|---|---|---|---|---|---|---|---|---|---|---|
| Val 545 | Ile | Arg | Gly | Pro | Glu 550 | Ile | Thr | Val | Gln 555 | Pro | Ala | Ala | Gln | Pro 560 Thr |
| Glu | Gln | Glu | Ser | Val 565 | Ser | Leu | Leu | Cys | Thr 570 | Ala | Asp | Arg | Asn 575 | Thr Phe |
| Glu | Asn | Leu | Thr 580 | Trp | Tyr | Lys | Leu | Gly 585 | Ser | Gln | Ala | Thr 590 | Ser | Val His |
| Met | Gly | Glu 595 | Ser | Leu | Thr | Pro | Val 600 | Cys | Lys | Asn | Leu 605 | Asp | Ala | Leu Trp |
| Lys | Leu | Asn 610 | Gly | Thr | Met | Phe 615 | Ser | Asn | Ser | Thr 620 | Asn | Asp | Ile | Leu Ile |
| Val 625 | Ala | Phe | Gln | Asn | Ala 630 | Ser | Leu | Gln | Asp 635 | Gln | Gly | Asp | Tyr | Val Cys 640 |
| Ser | Ala | Gln | Asp | Lys 645 | Lys | Thr | Lys | Lys | Arg 650 | His | Cys | Leu | Val | Lys Gln 655 |
| Leu | Ile | Ile | Leu 660 | Glu | Arg | Met | Ala | Pro 665 | Met | Ile | Thr | Gly 670 | Asn | Leu Glu |
| Asn | Gln | Thr 675 | Thr | Thr | Ile | Gly 680 | Glu | Thr | Ile | Glu | Val 685 | Thr | Cys | Pro Ala |
| Ser | Gly | Asn 690 | Pro | Thr | Pro | His 695 | Ile | Thr | Trp | Phe | Lys 700 | Asp | Asn | Glu Thr |
| Leu 705 | Val | Glu | Asp | Ser | Gly 710 | Ile | Val | Leu | Arg | Asp 715 | Gly | Asn | Arg | Asn Leu 720 |
| Thr | Ile | Arg | Arg | Val 725 | Arg | Lys | Glu | Asp | Gly 730 | Gly | Leu | Tyr | Thr 735 | Cys Gln |
| Ala | Cys | Asn | Val 740 | Leu | Gly | Cys | Ala | Arg 745 | Ala | Glu | Thr | Leu | Phe 750 | Ile Ile |
| Glu | Gly | Ala 755 | Gln | Glu | Lys | Thr | Asn 760 | Leu | Glu | Val | Ile 765 | Ile | Leu | Val Gly |
| Thr | Ala | Val 770 | Ile | Ala | Met | Phe 775 | Phe | Trp | Leu | Leu | Leu 780 | Val | Ile | Leu Val |
| Arg 785 | Thr | Val | Lys | Arg | Ala 790 | Asn | Glu | Gly | Glu | Leu 795 | Lys | Thr | Gly | Tyr Leu 800 |
| Ser | Ile | Val | Met | Asp 805 | Pro | Asp | Glu | Leu | Pro 810 | Leu | Asp | Glu | Arg | Cys Glu 815 |
| Arg | Leu | Pro | Tyr 820 | Asp | Ala | Ser | Lys | Trp 825 | Glu | Phe | Pro | Arg | Asp 830 | Arg Leu |
| Lys | Leu | Gly 835 | Lys | Pro | Leu | Gly | Arg 840 | Gly | Ala | Phe | Gly 845 | Gln | Val | Ile Glu |
| Ala | Asp 850 | Ala | Phe | Gly | Ile | Asp 855 | Lys | Thr | Ala | Thr | Cys 860 | Lys | Thr | Val Ala |
| Val 865 | Lys | Met | Leu | Lys | Glu 870 | Gly | Ala | Thr | His | Ser 875 | Glu | His | Arg | Ala Leu 880 |
| Met | Ser | Glu | Leu | Lys 885 | Ile | Leu | Ile | His | Ile 890 | Gly | His | His | Leu | Asn Val 895 |
| Val | Asn | Leu | Leu 900 | Gly | Ala | Cys | Thr | Lys 905 | Pro | Gly | Gly | Pro | Leu 910 | Met Val |
| Ile | Val | Glu 915 | Phe | Ser | Lys | Phe | Gly 920 | Asn | Leu | Ser | Thr 925 | Tyr | Leu | Arg Gly |
| Lys | Arg | Asn 930 | Glu | Phe | Val | Pro 935 | Tyr | Lys | Ser | Lys | Gly 940 | Ala | Arg | Phe Arg |
| Gln | Gly | Lys | Asp | Tyr 950 | Val | Gly | Glu | Leu | Ser 955 | Val | Asp | Leu | Lys | Arg Arg 960 |
| | | | | | | | | | | | | | | |
| Leu | Asp | Ser | Ile | Thr 965 | Ser | Ser | Gln | Ser | Ser 970 | Ala | Ser | Ser | Gly | Phe Val 975 |
| Glu | Glu | Lys | Ser | Leu | Ser | Asp | Val | Glu | Glu | Glu | Glu | Ala | Ser | Glu Glu |

-continued

```
              980                          985                          990
Leu Tyr Lys Asp Phe Leu Thr Leu Glu His Leu Ile Cys Tyr Ser Phe
        995                     1000                     1005
Gln Val Ala Lys Gly Met Glu Phe Leu Ala Ser Arg Lys Cys Ile His
       1010                    1015                    1020
Arg Asp Leu Ala Ala Arg Asn Ile Leu Leu Ser Glu Lys Asn Val Val
1025                    1030                    1035                    1040
Lys Ile Cys Asp Phe Gly Leu Ala Arg Asp Ile Tyr Lys Asp Pro Asp
        1045                    1050                    1055
Tyr Val Arg Lys Gly Asp Ala Arg Leu Pro Leu Lys Trp Met Ala Pro
        1060                    1065                    1070
Glu Thr Ile Phe Asp Arg Val Tyr Thr Ile Gln Ser Asp Val Trp Ser
       1075                    1080                    1085
Phe Gly Val Leu Leu Trp Glu Ile Phe Ser Leu Gly Ala Ser Pro Tyr
       1090                    1095                    1100
Pro Gly Val Lys Ile Asp Glu Glu Phe Cys Arg Arg Leu Lys Glu Gly
1105                    1110                    1115                    1120
Thr Arg Met Arg Ala Pro Asp Tyr Thr Thr Pro Glu Met Tyr Gln Thr
                1125                    1130                    1135
Met Leu Asp Cys Trp His Glu Asp Pro Asn Gln Arg Pro Ser Phe Ser
                1140                    1145                    1150
Glu Leu Val Glu His Leu Gly Asn Leu Leu Gln Ala Asn Ala Gln Gln
                1155                    1160                    1165
Asp Gly Lys Asp Tyr Ile Val Leu Pro Met Ser Glu Thr Leu Ser Met
       1170                    1175                    1180
Glu Glu Asp Ser Gly Leu Ser Leu Pro Thr Ser Pro Val Ser Cys Met
1185                    1190                    1195                    1200
Glu Glu Glu Glu Val Cys Asp Pro Lys Phe His Tyr Asp Asn Thr Ala
                1205                    1210                    1215
Gly Ile Ser His Tyr Leu Gln Asn Ser Lys Arg Lys Ser Arg Pro Val
            1220                    1225                    1230
Ser Val Lys Thr Phe Glu Asp Ile Pro Leu Glu Glu Pro Glu Val Lys
       1235                    1240                    1245
Val Ile Pro Asp Asp Ser Gln Thr Asp Ser Gly Met Val Leu Ala Ser
1250                    1255                    1260
Glu Glu Leu Lys Thr Leu Glu Asp Arg Asn Lys Leu Ser Pro Ser Phe
1265                    1270                    1275                    1280
Gly Gly Met Met Pro Ser Lys Ser Arg Glu Ser Val Ala Ser Glu Gly
                1285                    1290                    1295
Ser Asn Gln Thr Ser Gly Tyr Gln Ser Gly Tyr His Ser Asp Asp Thr
               1300                    1305                    1310
Asp Thr Thr Val Tyr Ser Ser Asp Glu Ala Gly Leu Leu Lys Met Val
        1315                    1320                    1325
Asp Ala Ala Val His Ala Asp Ser Gly Thr Thr Leu Gln Leu Thr Ser
1330                    1335                    1340
Cys Leu Asn Gly Ser Gly Pro Val Pro Ala Pro Pro Pro Thr Pro Gly
1345                    1350                    1355                    1360
Asn His Glu Arg Gly Ala Ala
                1365
```